(12) United States Patent
Duijsens et al.

(10) Patent No.: US 12,257,437 B2
(45) Date of Patent: Mar. 25, 2025

(54) INTRAVENOUS PHRENIC NERVE STIMULATION LEAD

(71) Applicant: Covidien LP, Mansfield, MA (US)

(72) Inventors: Victor Duijsens, Grevenbicht (NL); Abhijit Bhattacharya, Hyderabad (IN); Lilian Kornet, Eijsden (NL)

(73) Assignee: Covidien LP, Mansfield, MA (US)

( * ) Notice: Subject to any disclaimer, the term of this patent is extended or adjusted under 35 U.S.C. 154(b) by 1081 days.

(21) Appl. No.: 17/039,115

(22) Filed: Sep. 30, 2020

(65) Prior Publication Data

US 2022/0096843 A1 Mar. 31, 2022

(51) Int. Cl.
*A61N 1/36* (2006.01)
*A61M 16/00* (2006.01)
(Continued)

(52) U.S. Cl.
CPC ..... *A61N 1/36139* (2013.01); *A61M 16/0063* (2014.02); *A61M 16/024* (2017.08); *A61N 1/0551* (2013.01); *A61N 1/3615* (2013.01); *A61N 1/36171* (2013.01); *A61M 16/04* (2013.01); *A61M 16/0666* (2013.01); *A61M 2205/505* (2013.01); *A61M 2205/52* (2013.01);
(Continued)

(58) Field of Classification Search
CPC ............. A61N 1/36139; A61N 1/0551; A61M 2230/40
See application file for complete search history.

(56) References Cited

U.S. PATENT DOCUMENTS 3,584,621 A 6/1971 Bird et al.
3,586,021 A 6/1971 McGuinness
(Continued)

FOREIGN PATENT DOCUMENTS

| CN | 105916549 A * | 8/2016 | ........... A61B 5/0205 |
| WO | WO 10108552 | 9/2010 | |
| WO | WO-2014160832 A2 * | 10/2014 | ......... A61B 18/1492 |

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Tammie K Marlen
*Assistant Examiner* — Maria Catherine Anthony

(57) ABSTRACT

Aspects of this disclosure describe methods and systems for phrenic nerve stimulation using a stimulation lead placed in a blood vessel. The stimulation lead includes at least one deformable segment that has at least two configurations. For example, the deformable segment may have an elongate configuration and a non-elongate configuration. In the elongate configuration, the deformable segment may be substantially straight, thereby allowing placement of the stimulation lead using a catheter. In the non-elongate configuration, the deformable segment may be a circle or spiral. The deformable segment may transition from the elongate configuration to the non-elongate configuration after the stimulation lead is positioned in the vein. The stimulation lead may be fixated to the vein at a fixation element. Additionally, the stimulation lead may include electrodes distributed along the deformable segment and at least one elongate segment.

16 Claims, 12 Drawing Sheets

(51) Int. Cl.
*A61N 1/05* (2006.01)
*A61M 16/04* (2006.01)
*A61M 16/06* (2006.01)

(52) U.S. Cl.
CPC ... *A61M 2230/005* (2013.01); *A61M 2230/40* (2013.01); *A61M 2230/42* (2013.01)

(56) References Cited

U.S. PATENT DOCUMENTS

| | | |
|---|---|---|
| 3,633,576 A | 1/1972 | Gorsuch |
| 3,662,751 A | 5/1972 | Barkalow et al. |
| 3,664,370 A | 5/1972 | Warnow |
| 3,669,108 A | 6/1972 | Sundblom et al. |
| 3,695,263 A | 10/1972 | Kipling |
| 3,741,208 A | 6/1973 | Jonsson et al. |
| 3,753,436 A | 8/1973 | Bird et al. |
| 3,756,229 A | 9/1973 | Ollivier |
| 3,768,468 A | 10/1973 | Cox |
| 3,789,837 A | 2/1974 | Philips et al. |
| 3,834,382 A | 9/1974 | Lederman et al. |
| 3,889,669 A | 6/1975 | Weigl |
| 3,896,800 A | 7/1975 | Cibulka |
| 3,903,881 A | 9/1975 | Weigl |
| 3,905,362 A | 9/1975 | Eyrick et al. |
| 3,910,261 A | 10/1975 | Ragsdale et al. |
| 3,961,627 A | 6/1976 | Ernst et al. |
| 3,976,052 A | 8/1976 | Junginger et al. |
| 3,981,301 A | 9/1976 | Warnow et al. |
| 4,003,377 A | 1/1977 | Dahl |
| 4,029,120 A | 6/1977 | Christianson |
| 4,044,763 A | 8/1977 | Bird |
| 4,050,458 A | 9/1977 | Friend |
| 4,060,078 A | 11/1977 | Bird |
| 4,121,578 A | 10/1978 | Torzala |
| 4,155,357 A | 5/1979 | Dahl |
| 4,164,219 A | 8/1979 | Bird |
| 4,197,856 A | 4/1980 | Northrop |
| 4,211,221 A | 7/1980 | Schwanbom et al. |
| 4,275,722 A | 6/1981 | Sorensen |
| 4,281,651 A | 8/1981 | Cox |
| 4,323,064 A | 4/1982 | Hoenig et al. |
| 4,340,044 A | 7/1982 | Levy et al. |
| 4,351,344 A | 9/1982 | Stenzler |
| 4,401,115 A | 8/1983 | Monnier |
| 4,448,192 A | 5/1984 | Stawitcke et al. |
| 4,459,982 A | 7/1984 | Fry |
| 4,459,983 A | 7/1984 | Beyreuther et al. |
| 4,539,984 A | 9/1985 | Kiszel et al. |
| 4,554,916 A | 11/1985 | Watt |
| 4,558,710 A | 12/1985 | Eichler |
| 4,566,450 A | 1/1986 | Brossman, Jr. |
| 4,598,706 A | 7/1986 | Darowski et al. |
| 4,612,928 A | 9/1986 | Tiep et al. |
| 4,640,277 A | 2/1987 | Meyer et al. |
| 4,648,407 A | 3/1987 | Sackner |
| 4,757,824 A | 7/1988 | Chaumet |
| 4,766,894 A | 8/1988 | Legrand et al. |
| 4,796,618 A | 1/1989 | Garraffa |
| 4,889,116 A | 12/1989 | Taube |
| 4,981,295 A | 1/1991 | Belman et al. |
| 4,982,735 A | 1/1991 | Yagata et al. |
| 5,007,420 A | 4/1991 | Bird |
| 5,016,626 A | 5/1991 | Jones |
| 5,099,837 A | 3/1992 | Russel, Sr. et al. |
| 5,107,830 A | 4/1992 | Younes |
| 5,154,167 A | 10/1992 | Hepburn |
| 5,161,525 A | 11/1992 | Kimm et al. |
| 5,165,397 A | 11/1992 | Arp |
| 5,307,795 A | 5/1994 | Whitwam et al. |
| 5,316,009 A | 5/1994 | Yamada |
| 5,318,487 A | 6/1994 | Golen et al. |
| 5,323,772 A | 6/1994 | Linden et al. |
| 5,335,654 A | 8/1994 | Rapoport |
| 5,373,842 A | 12/1994 | Olsson et al. |
| 5,390,666 A | 2/1995 | Kimm et al. |
| 5,404,871 A | 4/1995 | Goodman et al. |
| 5,429,123 A | 7/1995 | Shaffer et al. |
| 5,433,193 A | 7/1995 | Sanders et al. |
| 5,458,137 A | 10/1995 | Axe et al. |
| 5,479,920 A | 1/1996 | Piper et al. |
| 5,487,383 A | 1/1996 | Levinson |
| 5,494,028 A | 2/1996 | DeVries et al. |
| RE35,295 E | 7/1996 | Estes et al. |
| 5,535,738 A | 7/1996 | Estes et al. |
| 5,540,220 A | 7/1996 | Gropper et al. |
| 5,549,655 A | 8/1996 | Erickson |
| 5,551,419 A | 9/1996 | Froehlich et al. |
| 5,564,416 A | 10/1996 | Jones |
| 5,582,163 A | 12/1996 | Bonassa |
| 5,603,315 A | 2/1997 | Sasso, Jr. |
| 5,632,269 A | 5/1997 | Zdrojkowski |
| 5,645,053 A | 7/1997 | Remmers et al. |
| 5,647,345 A | 7/1997 | Saul |
| 5,647,351 A | 7/1997 | Weismann et al. |
| 5,660,171 A | 8/1997 | Kimm et al. |
| 5,706,799 A | 1/1998 | Imai et al. |
| 5,720,277 A | 2/1998 | Olsson et al. |
| 5,727,562 A | 3/1998 | Beck |
| 5,735,267 A | 4/1998 | Tobia |
| 5,738,090 A | 4/1998 | Lachmann et al. |
| 5,740,796 A | 4/1998 | Skog |
| 5,752,509 A | 5/1998 | Lachmann et al. |
| 5,794,615 A | 8/1998 | Estes |
| 5,797,393 A | 8/1998 | Kohl |
| 5,803,065 A | 9/1998 | Zdrojkowski et al. |
| 5,803,066 A | 9/1998 | Rapoport et al. |
| 5,865,173 A | 2/1999 | Froehlich |
| 5,915,381 A | 6/1999 | Nord |
| 5,921,238 A | 7/1999 | Bourdon |
| 5,927,274 A | 7/1999 | Servidio et al. |
| 5,931,162 A | 8/1999 | Christian |
| 6,041,780 A | 3/2000 | Richard et al. |
| 6,044,841 A | 4/2000 | Verdun et al. |
| 6,066,101 A | 5/2000 | Johnson et al. |
| 6,076,519 A | 6/2000 | Johnson |
| 6,095,140 A | 8/2000 | Poon et al. |
| 6,099,481 A | 8/2000 | Daniels et al. |
| 6,138,675 A | 10/2000 | Berthon-Jones |
| 6,142,150 A | 11/2000 | O'Mahoney |
| 6,148,814 A | 11/2000 | Clemmer et al. |
| 6,158,432 A | 12/2000 | Biondi et al. |
| 6,158,433 A | 12/2000 | Ong et al. |
| 6,220,244 B1 | 4/2001 | McLaughlin |
| 6,230,708 B1 | 5/2001 | Radko |
| 6,253,765 B1 | 7/2001 | Hognelid et al. |
| 6,305,374 B1 | 10/2001 | Zdrojkowski et al. |
| 6,318,365 B1 | 11/2001 | Vogele et al. |
| 6,345,619 B1 | 2/2002 | Finn |
| 6,439,229 B1 | 8/2002 | Du et al. |
| 6,450,163 B1 | 9/2002 | Blacker et al. |
| 6,463,930 B2 | 10/2002 | Biondi et al. |
| 6,467,477 B1 | 10/2002 | Frank et al. |
| 6,484,719 B1 | 11/2002 | Berthon-Jones |
| 6,512,938 B2 | 1/2003 | Claure et al. |
| 6,526,970 B2 | 3/2003 | DeVries et al. |
| 6,526,974 B1 | 3/2003 | Brydon et al. |
| 6,532,957 B2 | 3/2003 | Berthon-Jones |
| 6,532,959 B1 | 3/2003 | Berthon-Jones |
| 6,533,730 B2 | 3/2003 | Stroem |
| 6,537,228 B1 | 3/2003 | Lambert |
| 6,539,940 B2 | 4/2003 | Zdrojkowski et al. |
| 6,553,992 B1 | 4/2003 | Berthon-Jones et al. |
| 6,575,163 B1 | 6/2003 | Berthon-Jones |
| 6,581,597 B2 | 6/2003 | Sugiura |
| 6,588,423 B1 | 7/2003 | Sinderby |
| 6,595,212 B1 | 7/2003 | Arnott |
| 6,601,583 B2 | 8/2003 | Pessala et al. |
| 6,622,725 B1 | 9/2003 | Fisher et al. |
| 6,622,726 B1 | 9/2003 | Du |
| 6,626,175 B2 | 9/2003 | Jafari et al. |
| 6,668,824 B1 | 12/2003 | Isaza et al. |
| 6,668,829 B2 | 12/2003 | Biondi et al. |
| 6,671,529 B2 | 12/2003 | Claure et al. |
| 6,688,307 B2 | 2/2004 | Berthon-Jones |

(56) References Cited

U.S. PATENT DOCUMENTS

| | | |
|---|---|---|
| 6,694,978 B1 | 2/2004 | Bennarsten |
| 6,722,360 B2 | 4/2004 | Doshi |
| 6,758,216 B1 | 7/2004 | Berthon-Jones et al. |
| 6,810,876 B2 | 11/2004 | Berthon-Jones |
| 6,823,866 B2 | 11/2004 | Jafari et al. |
| 6,863,068 B2 | 3/2005 | Jamison et al. |
| 6,863,656 B2 | 3/2005 | Lurie |
| 6,866,040 B1 | 3/2005 | Bourdon |
| 6,920,875 B1 | 7/2005 | Hill et al. |
| 6,920,878 B2 | 7/2005 | Sinderby et al. |
| 6,938,619 B1 | 9/2005 | Hickle |
| 6,948,497 B2 | 9/2005 | Zdrojkowski et al. |
| 6,988,498 B2 | 1/2006 | Berthon-Jones et al. |
| 6,990,980 B2 | 1/2006 | Richey, II |
| 7,000,612 B2 | 2/2006 | Jafari et al. |
| 7,008,380 B1 | 3/2006 | Rees et al. |
| 7,011,091 B2 | 3/2006 | Hill et al. |
| 7,011,092 B2 | 3/2006 | McCombs et al. |
| 7,017,574 B2 | 3/2006 | Biondi et al. |
| 7,066,175 B2 | 6/2006 | Hamilton et al. |
| 7,070,570 B2 | 7/2006 | Sanderson et al. |
| 7,077,132 B2 | 7/2006 | Berthon-Jones |
| 7,087,027 B2 | 8/2006 | Page |
| 7,089,932 B2 | 8/2006 | Dodds |
| 7,100,607 B2 | 9/2006 | Zdrojkowski et al. |
| 7,100,609 B2 | 9/2006 | Berthon-Jones et al. |
| 7,104,962 B2 | 9/2006 | Lomask et al. |
| 7,128,069 B2 | 10/2006 | Farrugia et al. |
| 7,137,389 B2 | 11/2006 | Berthon-Jones |
| 7,152,598 B2 | 12/2006 | Morris et al. |
| 7,152,604 B2 | 12/2006 | Hickle et al. |
| 7,211,049 B2 | 5/2007 | Bradley et al. |
| 7,267,652 B2 | 9/2007 | Coyle et al. |
| 7,275,540 B2 | 10/2007 | Bolam et al. |
| 7,276,031 B2 | 10/2007 | Norman et al. |
| 7,311,668 B2 | 12/2007 | Lurie |
| 7,334,578 B2 | 2/2008 | Biondi et al. |
| 7,367,337 B2 | 5/2008 | Berthon-Jones et al. |
| 7,390,304 B2 | 6/2008 | Chen et al. |
| 7,392,806 B2 | 7/2008 | Yuen et al. |
| 7,467,012 B1 | 12/2008 | Park et al. |
| 7,472,702 B2 | 1/2009 | Beck et al. |
| 7,487,774 B2 | 2/2009 | Acker |
| 7,532,939 B2 | 5/2009 | Sommer |
| 7,547,285 B2 | 6/2009 | Kline |
| 7,552,731 B2 | 6/2009 | Jorczak et al. |
| 7,556,038 B2 | 7/2009 | Kirby et al. |
| 7,588,033 B2 | 9/2009 | Wondka |
| 7,621,270 B2 | 11/2009 | Morris et al. |
| 7,682,312 B2 | 3/2010 | Lurie |
| 7,717,113 B2 | 5/2010 | Andrieux |
| 7,722,546 B2 | 5/2010 | Madaus et al. |
| 7,735,486 B2 | 6/2010 | Payne |
| 7,735,492 B2 | 6/2010 | Doshi et al. |
| 7,775,207 B2 | 8/2010 | Jaffe et al. |
| 7,793,656 B2 | 9/2010 | Johnson |
| 7,798,145 B2 | 9/2010 | Weismann et al. |
| 7,802,571 B2 | 9/2010 | Tehrani |
| 7,810,496 B2 | 10/2010 | Estes et al. |
| 7,810,497 B2 | 10/2010 | Pittman et al. |
| 7,810,498 B1 | 10/2010 | Patterson |
| 7,850,619 B2 | 12/2010 | Gavish et al. |
| 7,850,685 B2 | 12/2010 | Kunis |
| 7,866,318 B2 | 1/2011 | Bassin |
| 7,938,114 B2 | 5/2011 | Matthews et al. |
| 7,963,283 B2 | 6/2011 | Sinderby |
| 7,970,475 B2 | 6/2011 | Tehrani et al. |
| 7,984,712 B2 | 7/2011 | Soliman et al. |
| 7,992,564 B2 | 8/2011 | Doshi et al. |
| 7,997,271 B2 | 8/2011 | Hickle et al. |
| 8,021,308 B2 | 9/2011 | Carlson et al. |
| 8,021,309 B2 | 9/2011 | Zilberg |
| 8,257,351 B2 | 9/2012 | Stewart |
| 8,478,413 B2 | 7/2013 | Splett |
| 8,695,593 B2 | 4/2014 | Tehrani |
| 8,755,909 B2 | 6/2014 | Sommer |
| 8,897,879 B2 | 11/2014 | Splett |
| 9,533,113 B2 | 1/2017 | Lain |
| 10,194,978 B2 | 2/2019 | Coulombe |
| 10,245,399 B2 | 4/2019 | Martin |
| 10,300,232 B2 | 5/2019 | Bassin |
| 2002/0017301 A1 | 2/2002 | Lundin |
| 2002/0042564 A1 | 4/2002 | Cooper et al. |
| 2002/0042565 A1 | 4/2002 | Cooper et al. |
| 2003/0140925 A1 | 7/2003 | Sapienza et al. |
| 2003/0195571 A1 | 10/2003 | Burnes |
| 2003/0225339 A1 | 12/2003 | Orr et al. |
| 2004/0149282 A1 | 8/2004 | Hickle |
| 2004/0244804 A1 | 12/2004 | Olsen et al. |
| 2005/0039748 A1 | 2/2005 | Andrieux |
| 2005/0085865 A1 | 4/2005 | Tehrani |
| 2005/0085867 A1 | 4/2005 | Tehrani et al. |
| 2005/0085868 A1 | 4/2005 | Tehrani et al. |
| 2005/0279358 A1 | 12/2005 | Richey, II |
| 2006/0021618 A1 | 2/2006 | Berthon-Jones et al. |
| 2006/0122662 A1 | 6/2006 | Tehrani et al. |
| 2006/0142815 A1 | 6/2006 | Tehrani et al. |
| 2006/0196507 A1 | 9/2006 | Bradley |
| 2006/0196508 A1 | 9/2006 | Chalvignac |
| 2006/0241708 A1 | 10/2006 | Boute |
| 2006/0272642 A1 | 12/2006 | Chalvignac |
| 2007/0017518 A1 | 1/2007 | Farrugia et al. |
| 2007/0062532 A1 | 3/2007 | Choncholas |
| 2007/0062533 A1 | 3/2007 | Choncholas et al. |
| 2007/0068528 A1 | 3/2007 | Bohm et al. |
| 2007/0089738 A1 | 4/2007 | Soliman et al. |
| 2007/0101992 A1 | 5/2007 | Soliman et al. |
| 2007/0123792 A1 | 5/2007 | Kline |
| 2007/0129646 A1 | 6/2007 | Heinonen et al. |
| 2007/0157931 A1 | 7/2007 | Parker et al. |
| 2007/0181122 A1 | 8/2007 | Mulier |
| 2008/0000475 A1 | 1/2008 | Hill |
| 2008/0011301 A1 | 1/2008 | Qian |
| 2008/0033304 A1 | 2/2008 | Dalal et al. |
| 2008/0041383 A1 | 2/2008 | Matthews et al. |
| 2008/0060656 A1 | 3/2008 | Isaza |
| 2008/0091117 A1 | 4/2008 | Choncholas et al. |
| 2008/0110462 A1 | 5/2008 | Chekal et al. |
| 2008/0135044 A1 | 6/2008 | Freitag et al. |
| 2008/0163872 A1 | 7/2008 | Negele et al. |
| 2008/0168990 A1 | 7/2008 | Cooke et al. |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0202525 A1 | 8/2008 | Mitton et al. |
| 2008/0208281 A1 | 8/2008 | Tehrani et al. |
| 2008/0283060 A1 | 11/2008 | Bassin |
| 2008/0295837 A1 | 12/2008 | McCormick et al. |
| 2009/0007914 A1 | 1/2009 | Bateman |
| 2009/0013999 A1 | 1/2009 | Bassin |
| 2009/0038617 A1 | 2/2009 | Berthon-Jones et al. |
| 2009/0095297 A1 | 4/2009 | Hallett |
| 2009/0114223 A1 | 5/2009 | Bonassa |
| 2009/0137919 A1 | 5/2009 | Bar-Lavie et al. |
| 2009/0139522 A1 | 6/2009 | Thomson et al. |
| 2009/0205660 A1 | 8/2009 | Thomson et al. |
| 2009/0266360 A1 | 10/2009 | Acker et al. |
| 2009/0277448 A1 | 11/2009 | Ahlmén et al. |
| 2009/0301488 A1 | 12/2009 | Sun |
| 2009/0308393 A1 | 12/2009 | Luceros |
| 2010/0186744 A1 | 2/2010 | Bourdon |
| 2010/0076322 A1 | 3/2010 | Shrivastav et al. |
| 2010/0076323 A1 | 3/2010 | Shrivastav et al. |
| 2010/0089396 A1 | 4/2010 | Richard et al. |
| 2010/0108066 A1 | 5/2010 | Martin et al. |
| 2010/0116270 A1 | 5/2010 | Edwards et al. |
| 2010/0125227 A1 | 5/2010 | Bird |
| 2010/0024820 A1 | 7/2010 | Andrieux |
| 2010/0249584 A1 | 9/2010 | Albertelli |
| 2010/0252046 A1 | 10/2010 | Dahlström et al. |
| 2010/0258124 A1 | 10/2010 | Madaus et al. |
| 2010/0275920 A1 | 11/2010 | Tham et al. |
| 2010/0275921 A1 | 11/2010 | Schindhelm et al. |
| 2011/0017214 A1 | 1/2011 | Tehrani |

(56) References Cited

U.S. PATENT DOCUMENTS

| | | |
|---|---|---|
| 2011/0030686 A1 | 2/2011 | Wilkinson et al. |
| 2011/0073112 A1 | 3/2011 | DiBlasi et al. |
| 2011/0092841 A1 | 4/2011 | Bassin |
| 2011/0100365 A1 | 5/2011 | Wedler et al. |
| 2011/0112424 A1 | 5/2011 | Kesselman et al. |
| 2011/0112425 A1 | 5/2011 | Muhlsteff et al. |
| 2011/0132363 A1 | 6/2011 | Chalvignac |
| 2011/0160822 A1* | 6/2011 | Jackson ................ A61N 1/056 607/116 |
| 2011/0226248 A1 | 9/2011 | Duff et al. |
| 2019/0344034 A1 | 11/2019 | Li |
| 2020/0295231 A1 | 9/2020 | Meng |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Puritan Bennett 980 Series Ventilator Operator's Manual, Covidien, Jan. 29, 2014, Part. No. 10077893 A Jan. 2014, 506 pages.

* cited by examiner

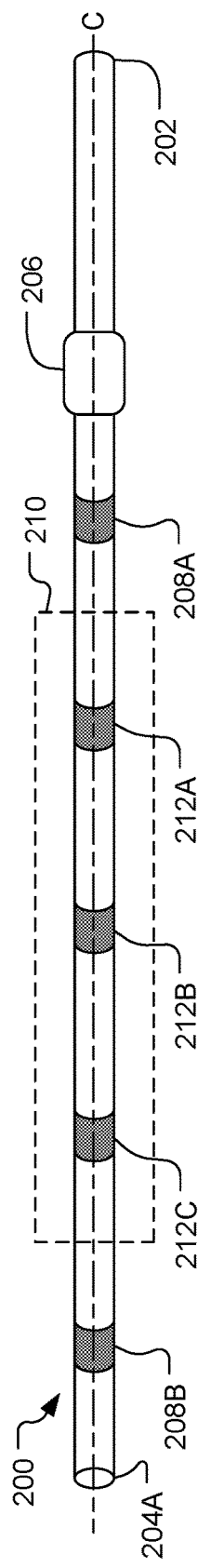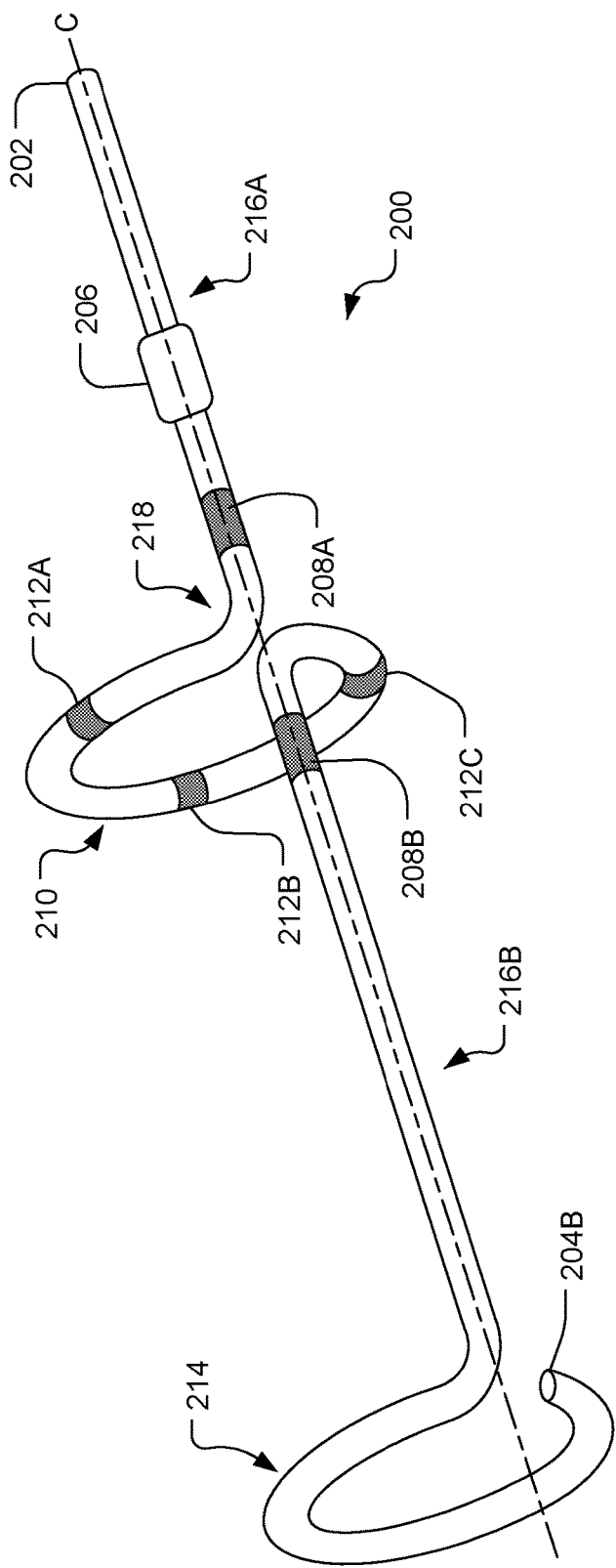

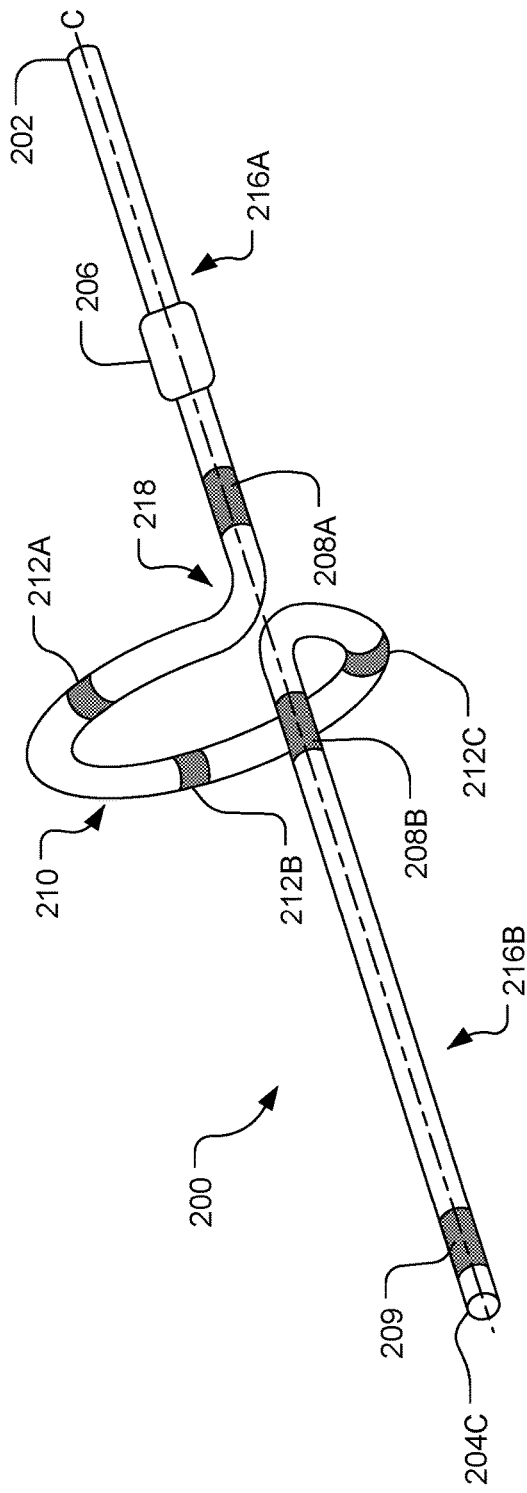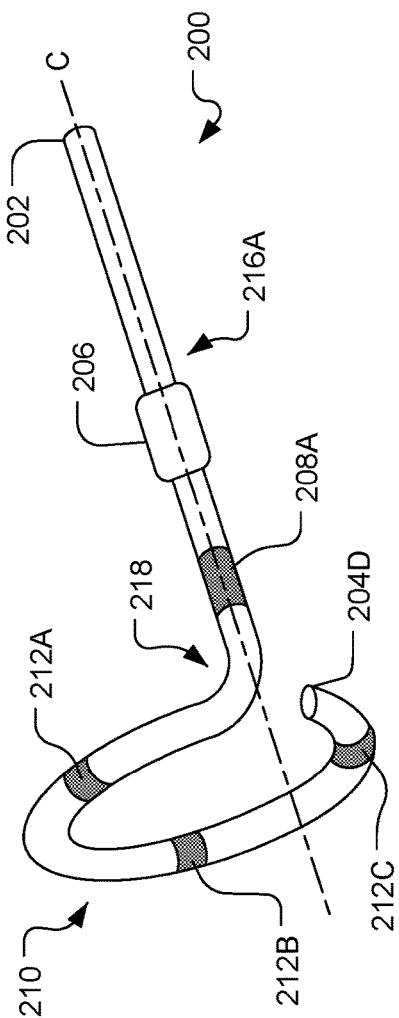
FIG. 2D
FIG. 2E

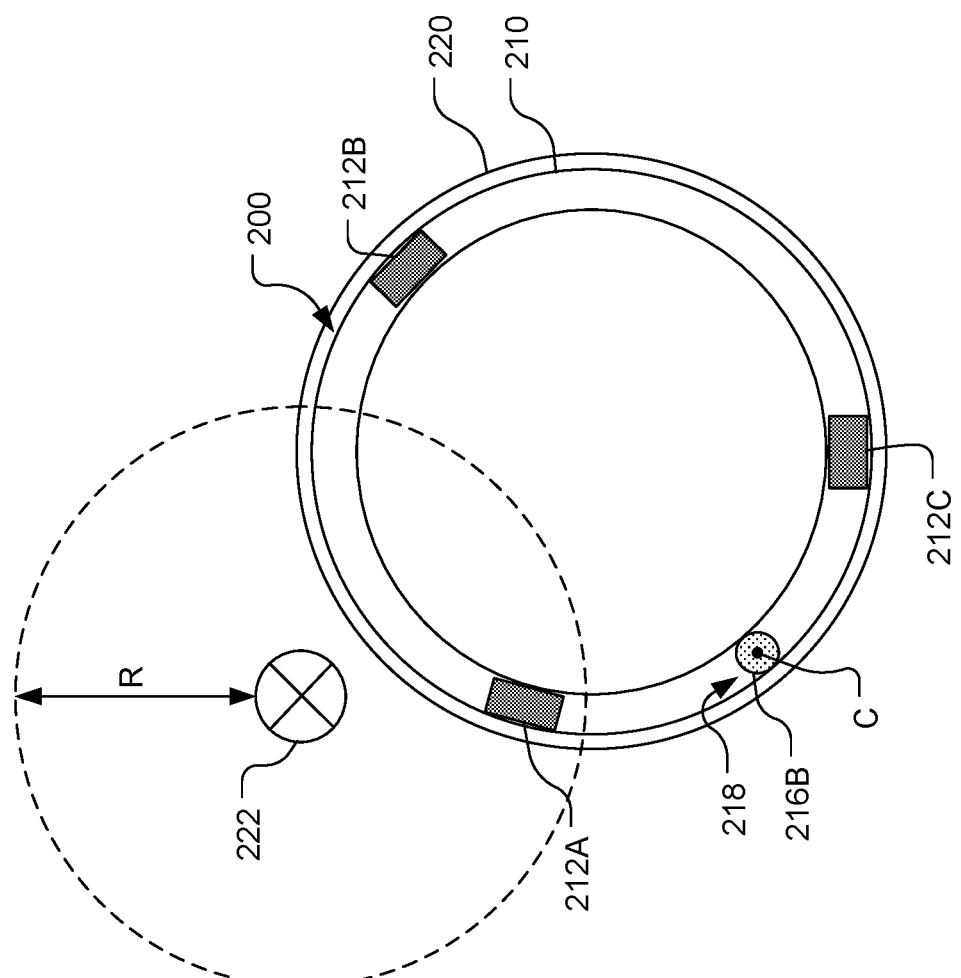

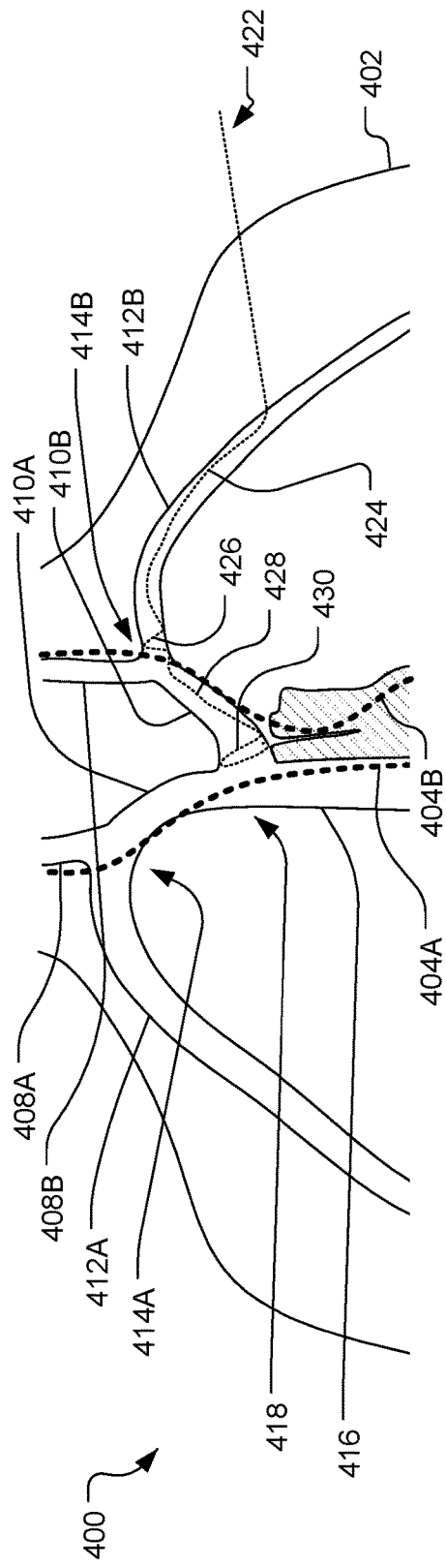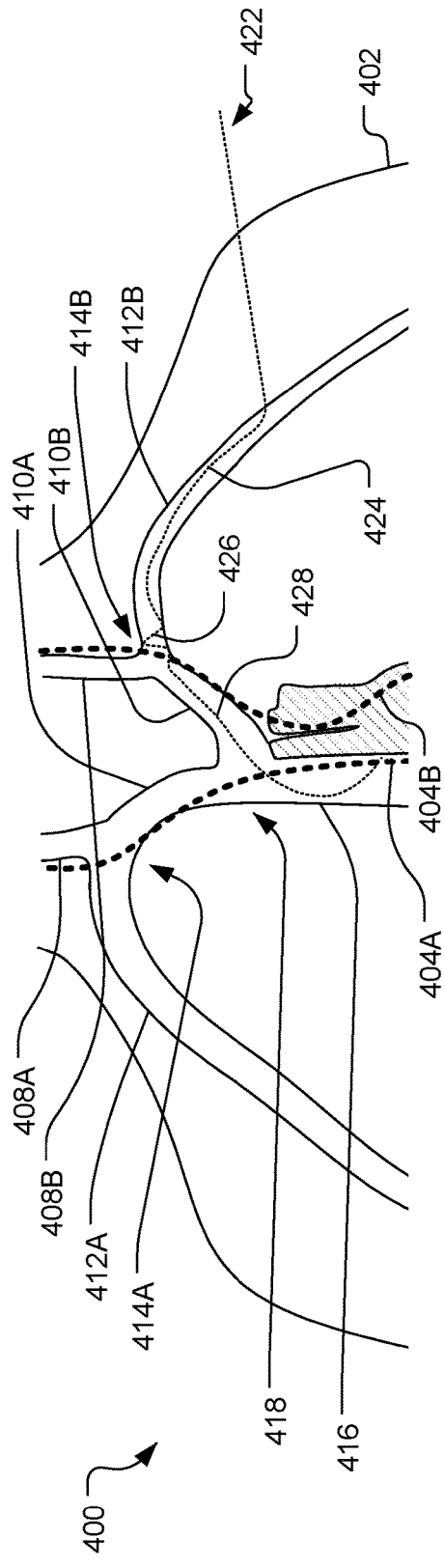

INTRAVENOUS PHRENIC NERVE STIMULATION LEAD

INTRODUCTION

Medical ventilator systems have long been used to provide ventilatory and supplemental oxygen support to patients. These ventilators typically comprise a connection for pressurized gas (air, oxygen) that is delivered to the patient through a conduit or tubing. As each patient may require a different ventilation strategy, modern ventilators can be customized for the particular needs of an individual patient. For example, several different ventilator modes or settings have been created to provide better ventilation for patients in different scenarios, such as mandatory ventilation modes, spontaneous ventilation modes, and assist-control ventilation modes. Ventilators monitor a variety of patient parameters and are well equipped to provide reports and other information regarding a patient's condition.

Long term external ventilation is typically provided to patients using positive pressure ventilation. Positive pressure ventilation is a form of artificial respiration in which a mechanical ventilator is used to deliver a controlled volume of gasses to the lungs of a patient. In contrast, in one form of negative-pressure ventilation, the diaphragm of a patient is caused to contract to cause the chest of the patient to expand during inspiration (thereby drawing air into the lungs), and the diaphragm is caused to relax to cause the chest to contract during exhalation (thereby forcing air out of the lungs). While lifesaving and valuable, positive pressure ventilation is non-physiological; that is, forcing air into the lungs is not the manner in which humans naturally breathe. Accordingly, the greater the positive pressure and/or the number of positive-pressure cycles, the more likely the patient will experience detrimental effects, such as an illness becoming more severe, ventilator-induced lung injury, acute respiratory distress syndrome (ARDS), ventilator-associated pneumonia (VAP), diaphragm dystrophy, and delay of ventilator weaning. These detrimental effects may increase an amount of time a patient is subjected to mechanical ventilation, leading to longer hospital stays and increased medical costs.

It is with respect to this general technical environment that aspects of the present technology disclosed herein have been contemplated. Furthermore, although a general environment is discussed, it should be understood that the examples described herein should not be limited to the general environment identified herein.

Among other things, aspects of the present disclosure include systems and methods for phrenic nerve stimulation with an intravenous stimulation lead. More specifically, this disclosure describes systems and methods for stimulating one or both phrenic nerves with a stimulation lead placed intravenously.

In an aspect, a stimulation lead for stimulating a phrenic nerve is disclosed. The stimulation lead includes a first elongate segment and a fixation element coupled to the first elongate segment. The fixation element is configured to removably couple the stimulation lead to an interior wall of a vein. The stimulation lead further includes a set of electrodes configured to stimulate the phrenic nerve and a first deformable segment coupled to the first elongate segment. The first deformable segment includes a first elongate configuration for placement of the stimulation lead in the vein, a first subset of electrodes of the set of electrodes, and a first non-elongate configuration wherein the first subset of electrodes are distributed radially inside the vein.

In an example, the first non-elongate configuration is one of: a circle or a helix. In another example, at least one portion of the first deformable segment is configured to contact an interior wall of the vein when the first deformable segment is in the first non-elongate configuration. In a further example, the first non-elongate configuration is a circle, the first subset of electrodes includes at least two electrodes, and the first subset of electrodes are evenly distributed about the first deformable segment. In yet another example, the first deformable segment is configured to transition between the first elongate configuration and the first non-elongate configuration. In still a further example, when the first deformable segment is in the first non-elongate configuration, the stimulation lead comprises a bend at the coupling of the first elongate segment and the first deformable segment.

In another example, the first elongate segment comprises at least one electrode of the set of electrodes. In a further example, the stimulation lead further includes: a second elongate segment; and a second deformable segment coupled to the second elongate segment, the second deformable segment including: a second elongate configuration for placement of the stimulation lead in the vein; and a second non-elongate configuration wherein at least one portion of the second deformable segment is configured to contact an interior wall of the vein when the second deformable segment is in the second non-elongate configuration. In yet another example, the first deformable segment is coupled to the first elongate segment and the second elongate segment. In still a further example, the second elongate segment comprises at least one electrode of the set of electrodes. In another example, no electrodes of the set of electrodes are included along the second deformable segment. In a further example, the first non-elongate configuration is one of: a circle or a helix.

In another aspect, a ventilator-implemented method for stimulating a phrenic nerve is disclosed. The method includes delivering ventilation to a patient according to ventilation settings and identifying a patient parameter. Based on the patient parameter and the initial ventilation settings, the method includes determining a nerve stimulation parameter. Additionally, the method includes causing delivery of a stimulating pulse to a phrenic nerve of the patient at a stimulation lead, based on the nerve stimulation parameter.

In an example, the method further includes identifying a change in the patient parameter; and based on the change in the patient parameter, adjusting the nerve stimulation parameter. In another example, the change in the patient parameter is associated with a change in the ventilation settings. In a further example, the stimulating pulse includes a stimulation frequency and an amount of stimulation each determined based on the patient parameter.

In a further aspect, a method for placing a stimulation lead in a vein is disclosed. The method includes positioning a stimulation lead in a vein with a catheter, the stimulation lead including: a set of electrodes; a first deformable segment in an elongate configuration; and a fixation element. Additionally, the method includes securing the stimulation lead to an interior wall of the vein at the fixation element. The method further includes transitioning the first deformable segment from the elongate configuration to a non-elongate configuration, wherein the non-elongate configuration distributes a first subset of electrodes of the set of electrodes radially inside the vein.

In an example, the method further includes causing delivery of a test pulse to the two test electrodes; and determining that the test pulse effectively stimulated a phrenic nerve. In another example, the method includes, after transitioning the first deformable segment to the non-elongate configuration, causing delivery of a stimulating pulse to the first subset of electrodes to stimulate a phrenic nerve proximate to the vein. In a further example, the stimulation lead further includes a second deformable segment without electrodes, and wherein the method further comprises transitioning the second deformable segment to the non-elongate configuration.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

FIGS. 2A-E show an example of an endovascular stimulation lead in two configurations, for phrenic nerve stimulation.

FIG. 2F shows an example cross-sectional view of a deformable segment of a stimulation lead with electrodes inside a blood vessel, proximate a phrenic nerve.

FIGS. 4A-B show an anatomy of a human patient with placement of a stimulation lead.

Figure 1:
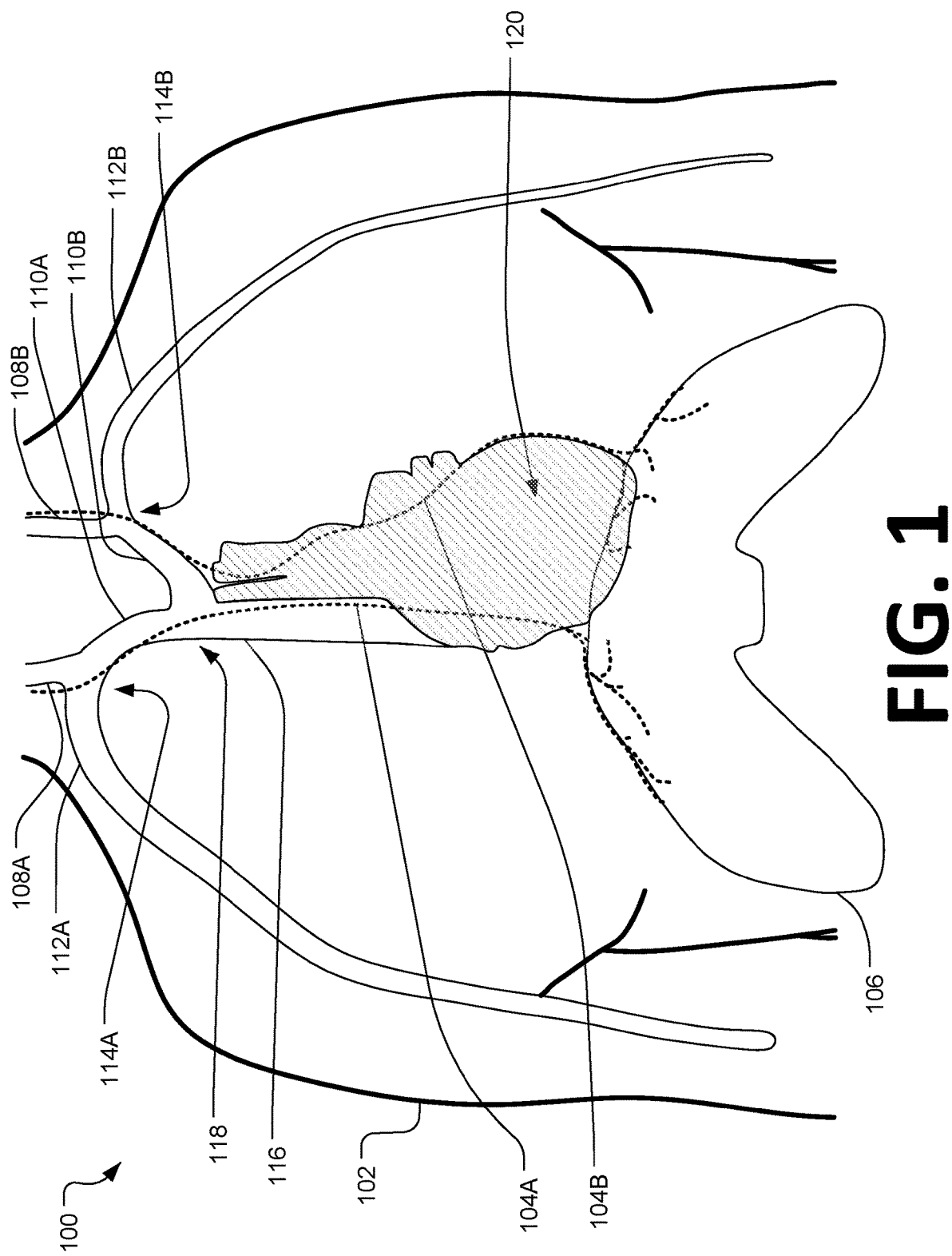
FIG. 1 shows an anatomy of a human patient, including phrenic nerves.

While examples of the disclosure are amenable to various modifications and alternative forms, specific aspects have been shown by way of example in the drawings and are described in detail below. The intention is not to limit the scope of the disclosure to the particular aspects described. On the contrary, the disclosure is intended to cover all modifications, equivalents, and alternatives falling within the scope of the disclosure and the appended claims.

DETAILED DESCRIPTION

As discussed briefly above, medical ventilators are used to provide breathing gases to patients who are otherwise unable to breathe sufficiently. In modern medical facilities, pressurized air and oxygen sources are often available from wall outlets, tanks, or other sources of pressurized gases. Accordingly, ventilators may provide pressure regulating valves (or regulators) connected to centralized sources of pressurized air and pressurized oxygen. The regulating valves function to regulate flow so that respiratory gases having a desired concentration are supplied to the patient at desired pressures and flow rates.

Approximately one third of patients in the intensive care unit depend on mechanical ventilation. With millions of people each year admitted to the intensive care unit, many people per year rely on mechanical ventilation. Additionally, respiratory illnesses such as COVID-19 increase the amount of individuals depending on mechanical ventilation. The amount of time a patient is assisted via mechanical ventilation may vary, as may be based on a lung condition of the patient. For example, approximately a third of patients with COPD or ARDS may seek assistance from a mechanical ventilator for longer than 4 days, with some patients requiring mechanical ventilation longer than seven days. Additionally, patients with sleep apnea may require mechanical ventilation while sleeping, over an extended period of time.

Weaning patients off of mechanical ventilation may be difficult. A patient's diaphragm muscles may begin to atrophy after as little as two days of ventilation. After a patient's diaphragm muscles begin to atrophy, a patient may require slow weaning to encourage the patient to breathe on their own (e.g., via the patient's diaphragm contracting unassisted by a mechanical ventilator). Increased time on a ventilator is associated with increased risk of infection, hyperventilation, hypoventilation, decreased venous return, and subsequent rehospitalization. Thus, minimizing a patient's time on a ventilator may be desirable for diaphragm health and/or to reduce the risk of infection and/or rehospitalization.

One solution is to exercise the patient's diaphragm muscles during ventilation to prevent or reduce the likelihood of diaphragm muscle atrophy and reduce the time that a patient is dependent on mechanical ventilation. To exercise a patient's diaphragm, the phrenic nerve can be stimulated with an electrical current. The electrical current to stimulate the phrenic nerve may be provided by a nearby stimulation lead. The stimulation lead may be placed inside of the body of the patient close enough to the phrenic nerve to stimulate the phrenic nerve. For example, the stimulation lead may be placed on or around the phrenic nerve or in a nearby blood vessel (e.g., vein, artery, arteriole, capillary, venule, etc.). Placement of the electrical lead, however, may cause complications. Some respiratory clinicians may not be skilled with placement of stimulation leads in the body, resulting in placement issues and/or complications. For example, stimulation leads attached on or around the phrenic nerve may pose a risk for inducing nerve damage during the installation or removal of the leads. Alternatively, stimulation leads placed in a blood vessel near the phrenic nerve may be difficult to position and/or secure in the blood vessel. Furthermore, improper placement and/or positioning of the stimulation lead inside of a blood vessel may not effectively stimulate the phrenic nerve or may fail to stimulate the phrenic nerve at all. For example, a stimulation lead laying inside a blood vessel opposite the phrenic nerve may not effectively stimulate the phrenic nerve. In another example, if the stimulation lead is not secured within the blood vessel, then movement of the lead inside the blood vessel may prevent or reduce stimulation of the phrenic nerve. A stimulation lead placed in an artery may have a higher risk of thrombosis than a stimulation lead placed intravenously. Intravenous placement may therefore be preferable.

Pacing therapy of a phrenic nerve (sometimes referred to as phrenic nerve pacing or diaphragm pacing, by stimulating the phrenic nerve thereby causing the phrenic nerve to send an electrical impulse to the diaphragm) may prevent or reverse diaphragm muscle-disuse atrophy, maintain diaphragmatic endurance, and facilitate weaning of patients from mechanical ventilation. Additionally, the paced diaphragm is expected to restore negative-pressure ventilation, thereby potentially providing a more physiological respiratory pattern and reducing the levels of positive pressure ventilation and its harmful effects on the lungs. Moreover, keeping the diaphragm active retains a patient's ability to cough, which reduces secretion and infection. Additionally or alternatively, phrenic nerve pacing may be utilized with patients experiencing chronic spinal injury or other injury that may benefit from pacing a few hours per day (or otherwise infrequently or non-continuously). Permanent or semi-permanent implantation is possible.

Aspects of this disclosure describe a minimally invasive stimulation lead system capable of effectively pacing the phrenic nerve. The pacing therapy may be administered by a mechanical ventilator such that pacing therapy may be administered while a patient is being ventilated. Aspects of this disclosure describe methods and systems for phrenic nerve stimulation using a stimulation lead. The stimulation lead is configurable so that at least one deformable segment can transition between an elongate configuration and a non-elongate configuration during installation or implantation. The stimulation lead is in a shaped configuration when one or more deformable segments are in a non-elongate configuration. In an example, the stimulation lead is placed intravenously. The stimulation lead includes at least one deformable segment that has at least two configurations. For example, the deformable segment may have an elongate configuration and a non-elongate configuration. In the elongate configuration, the deformable segment may be substantially straight, thereby allowing placement of the stimulation lead using a catheter. In the non-elongate configuration, the deformable segment may be a circle or spiral. The deformable segment may transition from the elongate configuration to the non-elongate configuration after the stimulation lead is positioned in the vein. The stimulation lead may be fixated to the vein at a fixation element. Additionally, the stimulation lead may include electrodes distributed along the deformable segment and at least one elongate segment.

FIG. 1 shows an anatomy of a human patient 100, including phrenic nerves (i.e., right phrenic nerve 104A and left phrenic nerve 104B). The body 102 of the patient 100 includes a right phrenic nerve 104A, a left phrenic nerve 104B, a diaphragm 106, a right internal jugular vein 108A, a left internal jugular vein 108B, a right brachiocephalic vein 110A, a left brachiocephalic vein 110B, a right subclavian vein 112A, a left subclavian vein 112B, a right jugular-brachiocephalic junction 114A, a left jugular-brachiocephalic junction 114B, a superior vena cava (SVC) 116, an SVC junction 118, and a heart 120. It should be appreciated that, although not shown, the body 102 of the patient 100 contains other anatomical structures.

The right phrenic nerve 104A and the left phrenic nerve 104B originate from the spinal cord in the neck region (C3-C5 cervical vertebral region). The right phrenic nerve 104A extends through the body 102 from the right side of the neck region between the right lung and the heart 120 to the right side of the diaphragm 106. The left phrenic nerve 104B extends through the body 102 from the left side of the neck region between the left lung and the heart 120 to the left side of the diaphragm 106. The right phrenic nerve 104A and the left phrenic nerve 104B may each, independently, send motor information to the diaphragm 106 using an electrical signal. The phrenic nerve is "stimulated" when the phrenic nerve sends an electrical signal to the diaphragm 106. To "effectively stimulate" the phrenic nerve, one or more muscles of the diaphragm 106 move (such as stiffening or contracting) due to the electrical signal sent from the phrenic nerve. The electrical signal to stimulate the phrenic nerve may originate naturally from the brain or may be provided artificially (e.g., by a nearby electrical current, and resulting magnetic field, from a stimulation lead). For example, the right phrenic nerve 104A and/or the left phrenic nerve 104B may be artificially stimulated by a magnetic field resulting from an electrical current between one or more electrodes on a stimulation lead. As an artificial magnetic field is created near the phrenic nerve, transmission fibers of the phrenic nerve are excited to create movement of muscles in the diaphragm. For the magnetic field to effectively stimulate the phrenic nerve, the one or more electrodes carrying the electrical current should be placed near, adjacent, or proximate the right phrenic nerve 104A and/or the left phrenic nerve 104B.

The motor information sent to the diaphragm 106 at the right phrenic nerve 104A and/or the left phrenic nerve 104B causes movement of one or more muscles of the diaphragm 106. Muscle movement of the diaphragm may cause the expansion of the lungs of the patient. For example, stimulation of the right phrenic nerve 104A causes one or more muscles on a right portion of the diaphragm 106 to move, thereby causing expansion of one or both lungs of the patient 100. In another example, stimulation of the left phrenic nerve 104B causes one or more muscles on a left portion of the diaphragm 106 to move, thereby causing expansion of one or both lungs of the patient 100. Stimulation of only one of the phrenic nerves (i.e., right phrenic nerve 104A or left phrenic nerve 104B) may cause muscle movement on both sides of the diaphragm, due to the collective nature of the diaphragm muscles (e.g., stimulating muscles on one side will also move some of the muscles on the other side). For some patients, stimulation of only one of the phrenic nerves is sufficient, while other patients may require or desire stimulation of both phrenic nerves. Examples of stimulating one or both phrenic nerves to obtain tidal volumes are provided in U.S. patent application Ser. No. 16/888,960, titled "Achieving Smooth Breathing by Modified Bilateral Phrenic Nerve Pacing" and filed on Jun. 1, 2020, which is incorporated herein by reference in its entirety.

In an example, a phrenic nerve (e.g., the right phrenic nerve 104A and/or left phrenic nerve 104B) may be stimulated by a magnetic field caused by a current between two or more electrodes. The electrodes may be positioned inside one or more blood vessels that run proximate to the phrenic nerve, such that the phrenic nerve is inside the resulting magnetic field. For example, electrodes may be positioned in one or more of the right internal jugular vein 108A, left internal jugular vein 108B, right brachiocephalic vein 110A, left brachiocephalic vein 110B, right subclavian vein 112A, left subclavian vein 112B, or superior vena cava (SVC) 116. The one or more electrodes may be placed on or along one or more stimulation leads, as described herein.

Figure 2C:
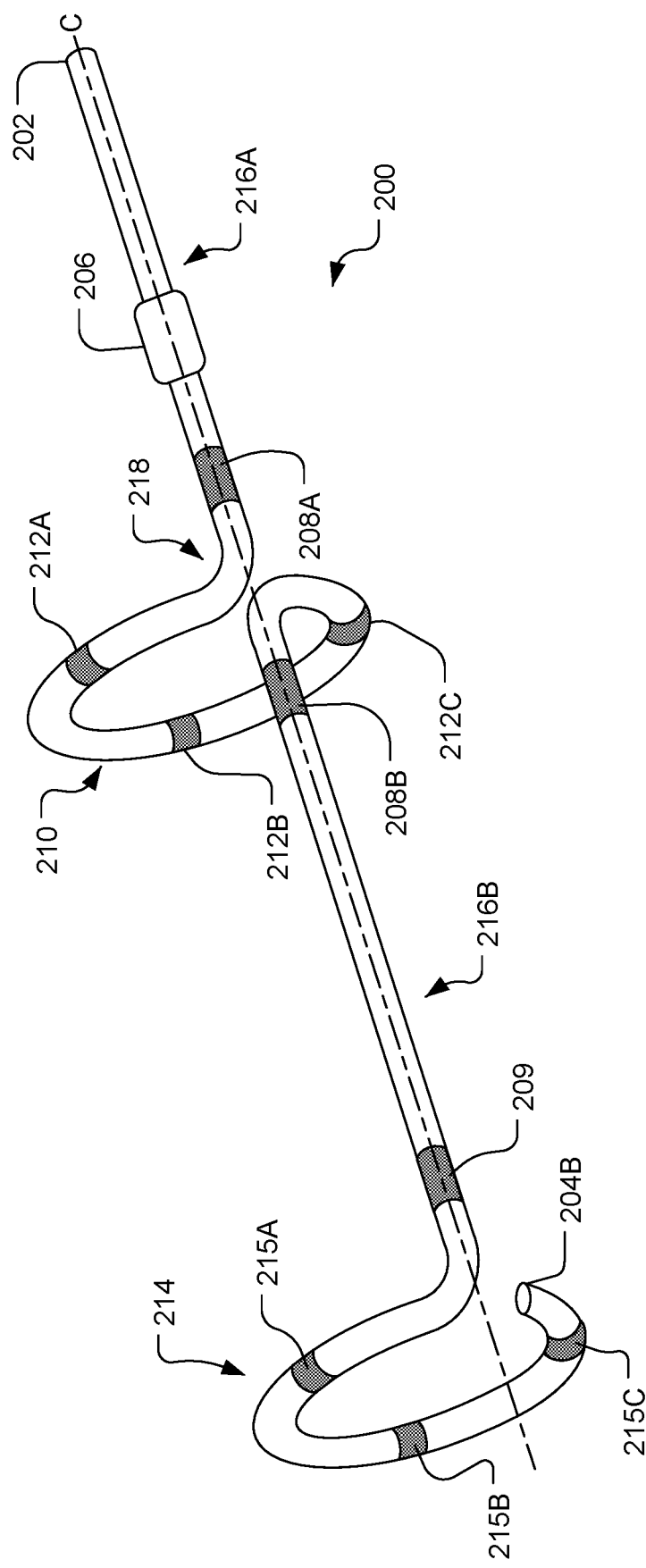

FIGS. 2A-E show an example of an endovascular stimulation lead 200 in two configurations (e.g., an elongate configuration shown in FIG. 2A and shape configuration shown in FIGS. 2B-E), for phrenic nerve stimulation. As referred to herein, the stimulation lead 200 is in a shape configuration when one or more deformable segments 210, 214 are in a non-elongate configuration. The examples shown depict a stimulation lead 200 in an elongate configuration that is substantially straight from the first end 202 to the second end 204A. Additionally, as shown, the stimulation lead 200 in the shape configuration has one or more non-elongate segments (otherwise referred to as deformable segments) between the first end 202 and the second end 204B-D. For example, two deformable segments 210, 214 are shown between the first end 202 and second end 204B of FIGS. 2B-C. Alternatively, FIGS. 2D-C show one deformable segment 210 between the first end 202 and the second end 204C, 204D. A second elongate portion 216B may extend between the deformable segment 210 and the second end 204C.

The stimulation lead 200 in the elongate configuration in FIG. 2A includes a first end 202, a second end 204A, a fixation element 206, a first deformable segment 210, and electrodes 208A-B, 212A-C. The first end 202 may protrude from the body of the patient or may be inside the body. In an example, the first deformable segment 210 is positioned inside the body of the patient near or proximate a phrenic nerve. The second end 204A extends past the phrenic nerve that is adjacent to the first deformable segment 210. A deformable segment is referred to herein as a portion of the stimulation lead that may transition from an elongate configuration to a non-elongate configuration. Different deformable segments may have different non-elongate configurations. As shown, the first deformable segment 210 includes electrodes 212A-C. Although three electrodes 212A-C are shown in the first deformable segment 210 of FIG. 2A, it should be appreciated that any number of electrodes may be included in the first deformable segment. Additionally, although one electrode 208A is shown along the first elongate segment 216A, it should be appreciated that any number of electrodes may be included in the first elongate segment 216A. Likewise, although one electrode 208B is shown along the second elongate segment 216B, it should be appreciated that any number of electrodes may be included in the second elongate segment 216B.

In an example where one electrode is included in the first deformable segment 210, the electrode may be positioned about the first deformable segment 210 opposite the first elongate segment 216A and/or second elongate segment 216B of the stimulation lead 200 in the shape configuration. In another example, a single electrode of the first deformable segment 210 may be positioned opposite an electrode 208A, 208B on the first elongate segment 216A or second elongate segment 216B.

A second deformable segment 214 may not include electrodes, as shown in FIG. 2B. Additionally or alternatively, adjacent portions of the stimulation lead may not include electrodes. For example, a second elongate segment 216B of the stimulation lead coupled to the second deformable segment 214 may not include electrodes. Alternatively, the second deformable segment 214 may include electrodes 215A-C, as shown in FIG. 2C. In an example, the second deformable segment 214 may have the same or similar electrode configuration as first deformable segment 210. In another example, the second deformable segment 214 may include electrodes 215A-C in a different quantity and/or configuration than the first deformable segment 210 (e.g., 2-12 electrodes 215A-C). Additionally, one or more electrodes 208B, 209 may be positioned along the second elongate portion 216B between the first deformable segment 210 and the second deformable segment 214. Although two deformable segments are shown (e.g., first deformable segment 210 and second deformable segment 214), it should be appreciated that the stimulation lead may include any number of deformable segments with any shape at any point along the stimulation lead.

The deformable segments 210, 214 of the stimulation lead 200 may be made of a shape-memory polymer capable of returning to an original shape after being deformed to a temporary shape. Electrodes 208A-B, 212A-C along the stimulation lead 200 may be made of an electrically conductive material. In an example, the non-elongate configuration of the deformable segments 210, 214 may be the original shape of the deformable segments 210, 214, and the elongate configuration may be the temporary shape. The shape-memory polymer may be induced into the temporary shape (e.g., the elongate shape) using a variety of inducers such as temperature, light, chemical agent, magnetic field, mechanical force, etc. For example, a stiff stylet may be inserted into an inner lumen of the stimulation lead 200 to straighten one or more deformable segments 210, 214 into their elongate configuration. The stylet may be made of a stiff material such as stainless steel or tungsten.

While the stylet is inserted into the stimulation lead 200, the stimulation lead 200 may be positioned inside the body of the patient. In an example, the stimulation lead 200 in the elongate configuration is placed inside the body proximate a phrenic nerve, while the stiff stylet is inserted into the stimulation lead 200. After removing the stylet from the stimulation lead 200 (otherwise referred to herein as pulling back the stylet, or retracting the stylet), the deformable segments 210, 214 of the stimulation lead 200 returns to the shape configuration. The stylet may be complete retracted from the stimulation lead 200, or may only be partially pulled back. The shape of the deformable segment 210, 214 may be based on how far the stylet is retracted. For example, the amount of retraction of the stylet may be controlled to result in different non-elongate shapes of the deformable segment 210, 214. The stimulation lead 200 in the shape configuration may be implanted into the body. Examples of catheters for use in ablation utilizing a lead with shaped portions are provided in U.S. Pat. No. 8,257,351, titled "Ablation Catheter Assembly with Radially Decreasing Helix and Method of Use" and filed on Apr. 15, 2010, and U.S. Pat. No. 7,850,685, titled "Ablation Catheter" and filed on Jun. 20, 2006, which are each incorporated herein by reference in their entireties.

A fixation element 206 may assist in placement of the stimulation lead 200 in the body of the patient. The fixation element may be used to secure the stimulation lead 200 in the elongate configuration, prior to configuring the stimulation lead 200 to the shape configuration, or in the shape configuration. In an example, the fixation element 206 may safely secure, or provide stability for, a portion of the stimulation lead to a wall of a blood vessel inside the body of the patient. By securing or increasing stability, the fixation element 206 prevents unwanted movement of the stimulation lead out of a targeted location in the body. If the stimulation lead moves outside of a targeted location, the electrodes 208A-B, 212A-C may not be close enough to the phrenic nerve to effectively stimulate the phrenic nerve. If the phrenic nerve is not effectively stimulated, one or more muscles in the diaphragm may not move as desired. At least one fixation element 206 may be included along the stimulation lead any elongate segment (e.g., first elongate segment 216A and/or second elongate segment 216B). The fixation element 206 may fixate to the wall of the blood vessel by biting in the wall, adhering to the wall, increasing friction with the wall, or other means of affixing to the wall of the blood vessel. Examples of active fixation leads are provided in U.S. Pat. No. 7,532,939, titled "Active Fixation Medical Lead" and filed on Jul. 21, 2005, and U.S. Pat. No. 8,755,909, titled "Active Fixation Medical Electrical Lead" and filed on Mar. 11, 2013, which are each incorporated herein by reference in their entireties.

The stimulation lead is positioned inside the body of the patient near a phrenic nerve. In an example, the stimulation lead is placed in a blood vessel that is proximate a phrenic nerve. The stimulation lead may be positioned across multiple blood vessels such that the first deformable segment 210 is positioned proximate the phrenic nerve. In an example, at least a portion of the stimulation lead, including the first deformable segment 210, is positioned inside the right brachiocephalic vein or the left brachiocephalic vein. Placement of the stimulation lead inside the body of the patient is further described herein.

The stimulation lead 200 in the elongate configuration may be positioned inside the body prior to transitioning the stimulation lead 200 to the shape configuration. For proper positioning, the stimulation lead may be moved inside the body while the stimulation lead provides an electrical current and resulting magnetic field, until the diaphragm muscles move due to stimulation of the phrenic nerve. After positioning the stimulation lead 200 inside the body in the elongate configuration, one or more deformable segments of the stimulation lead 200 may be transitioned (e.g., by retracting a stylet), thereby resulting in the stimulation lead 200 transitioning into a shape configuration. The stimulation lead 200 in the elongate configuration may be secured to a blood vessel wall inside the body at the fixation element 206 before transitioning the stimulation lead 200 to the shape configuration. As shown, the stimulation lead 200 in the shape configuration includes a first deformable segment 210 and a second deformable segment 214. It should be appreciated that the stimulation lead may have any number of deformable segments (e.g., one deformable segment or three deformable segments).

Additionally or alternatively, different deformable segments may transition to their non-elongate configurations independently (e.g., at different times or in different orders). For example, the deformable segments 210, 214 may transition to the non-elongate configuration during or after a stylet is retracted from that segment of the stimulation lead 200. Non-elongate configurations include shapes such as a circle, helix, spiral, polygon, rounded shape, edged shape, or any other shape that is not substantially linear. The non-elongate configuration of a deformable segment 210, 214 may lie on a plane. In other examples, the non-elongate configuration of a deformable segment may be non-planar (e.g., a spiral or a helix). One or more deformable segments may be configured to contact an interior wall of a blood vessel when in a shape configuration. For example, as shown in FIGS. 2A-F, the first deformable segment 210 is shaped into a substantially planar circle along the stimulation lead 200 in the shape configuration.

A non-elongate shape of the first deformable segment 210 may target a phrenic nerve better than an elongate shape. A phrenic nerve may be effectively stimulated when in the presence of a magnetic field. For a given current between at least two electrodes (e.g., electrodes 208A-B, 212A-C), the phrenic nerve will be effectively stimulated within a stimulation radius of the electrical current (e.g., stimulation radius R shown in FIG. 3). By distancing the electrodes 212A-C from the center line C of the elongate segments of the stimulation lead, the current travelling between two or more electrodes 212A-C is more likely to be within the stimulation radius of the phrenic nerve. For example, the stimulation lead may be fixated to an interior wall of a blood vessel at the fixation element 206 with the phrenic nerve located outside of the blood vessel and opposite from the point of fixation. In an instance, electrodes 208A-B (positioned along the center line C) may not produce an electrical current and resulting magnetic field to effectively stimulate the phrenic nerve. In another instance, one or more electrodes 212A-C positioned along the first deformable segment 210 and distanced from the center line C may produce an electrical current and resulting magnetic field to effectively stimulate the phrenic nerve.

Additionally, a deformable segment (e.g., first deformable segment 210 and/or second deformable segment 214) may be configured to contact an interior wall of the blood vessel at multiple points. For example, the deformable segment may contact the interior wall of the blood vessel in at least one point when the stimulation lead 200 is in the shape configuration. Additional points of contact of the deformable segment with the interior wall of the blood vessel may provide additional stability of the stimulation lead 200 when in the shape configuration inside the blood vessel (e.g., in addition to stability provided by the fixation element). In an example, when the stimulation lead 200 in the shape configuration is positioned inside of a blood vessel, all of the first deformable segment 210 contacts the interior wall of the blood vessel. In another example, one or more portions of the deformable segment of the stimulation lead 200 configured in the shape configuration may to contact the interior wall of the blood vessel.

In an example, when the first deformable segment 210 is in the non-elongate configuration, the stimulation lead 200 may include a bend 218. The bend 218 may promote fixation of the stimulation lead 200 in the shape configuration in a blood vessel by positioning the fixation element 206 adjacent to the interior wall of the blood vessel. The fixation element 206 may have increased contact with the interior wall of the blood vessel when positioned adjacent to the interior wall of the blood vessel prior to fixation.

FIG. 2F shows an example cross-sectional view of a deformable segment 210 of the stimulation lead 200 with electrodes 212A-C inside a blood vessel 220, proximate a phrenic nerve 222. The blood vessel 220 may be a vein, artery, arteriole, capillary, venule, etc. In a specific example, the blood vessel 220 is a vein, a portion of which is proximate a phrenic nerve 222. As shown, the deformable segment 210 of the stimulation lead 200 may be circular in shape to distribute electrodes 212A-C inside the blood vessel 220. In an example, the deformable segment 210 of the stimulation lead may position one or more electrodes 212A-C adjacent to the interior wall of the blood vessel 220. For example, the deformable segment 210 has a non-elongate shape to position electrodes 212A-C radially inside the blood vessel 220, outward from the center line C of an elongate segment 216B at bend 218. In another example, the non-elongate shape of the deformable segment 210 is configured to position at least one of the electrodes 212A-C adjacent to the phrenic nerve 222 (e.g., closer to the phrenic nerve than another electrode on the stimulation lead 200).

One or more attributes of each electrode 208A-B, 212A-C may be unique and/or independently controllable. For example, attributes of each electrode may include polarity, pulse length, pulse frequency, amplitude, etc. To cause an electrical current, two or more electrodes may be assigned opposite polarities. The electrodes may independently communicatively coupled and/or electrically coupled to one or more controllers. The controller may be electrically coupled to a power source. When voltage is applied, a current flows between the at least two electrodes. A power source may be an external battery that may be replaceable and/or rechargeable, or the power source may be shared with an external device (e.g., a power source of a ventilator). For example, the stimulation lead may be electrically coupled to an external device that provides power to the electrodes on the stimulation lead. In an example, a ventilator may provide power to the stimulation lead while contemporaneously ventilating a patient.

The phrenic nerve 222 may be effectively stimulated by a magnetic field resulting from a current running between electrodes 212A-C, when the current travels inside a stimulation radius R of the phrenic nerve 222. The current between two or more electrodes 212A-C may be increased or decreased as required or desired. An increase in current may increase the amount of stimulation of the phrenic nerve 222 and/or increase the stimulation radius of the phrenic nerve. A decrease in current may decrease the amount of stimulation of the phrenic nerve 222 and/or decrease the stimulation radius of the phrenic nerve. The amount of stimulation of the phrenic nerve 222 may be changed based on patient efforts and/or desired or determined tidal volume. A stimulation pulse along two or more electrodes 212A-C may be delivered over a pulse period to thereby cause stimulation of the phrenic nerve 222 during the pulse period. In an example, delivery of the stimulation pulse may be coordinated with delivery of an inhalation phase of ventilation provided by a mechanical ventilator (sometimes referred to as inhalation pacing).

In an example, electrodes 208A-B, 212A-C that are positioned adjacent to each other along the length of the stimulation lead may be assigned opposite polarities (positive and negative). Alternatively, two or more adjacent electrodes 208A-B, 212A-C may be assigned the same polarity. In an instance, at least one remaining electrode 212A-C is assigned the opposite polarity. The electrodes 208A-B, 212A-C may be assigned charges and polarities to be interphasic (with charge accumulation inside the blood vessel) or biphasic (little to no charge accumulation inside the blood vessel).

An initialization technique may be performed to optimize one or more attributes of each electrode. The initialization technique may test a variety of attributes of each electrode in variety of combinations. The optimization of attributes may be based on the amount of stimulation of the phrenic nerve or the tidal volume of the patient during phrenic nerve stimulation. In an example, a subset of the electrodes 208A-B, 212A-C may not be assigned an attribute (e.g., may not be used to stimulate the phrenic nerve). The initialization technique may be performed manually or using a predetermined program while monitoring the effort on the patient to determine the optimum settings.

In an example, an initialization technique may be carried out as follows. During or after placement of the stimulation lead in the body, one or more different subsets of electrodes 212A-C are separately pulsed and the effect is observed and stored. After the subsets of electrodes 212A-C have been pulsed, their effects on stimulation of the phrenic nerve are compared. In an example, the comparison may include an amount of diaphragm muscle movement and/or relative tidal volumes cause by the phrenic nerve stimulation. A subset of electrodes with a large effect (e.g., large amount of diaphragm muscle movement and/or large tidal volume) are identified. The identified subset of electrodes 212A-C may be used to stimulate the phrenic nerve. In an example, a subset of electrodes may be determined to effectively stimulate the phrenic nerve 222 when delivering a stimulation pulse (e.g., electrodes 212A and 212B or electrodes 212A and 212C).

As described herein, a phrenic nerve 222 is stimulated by a magnetic field resulting from an electrical current between two or more electrodes. Thus, the subset of stimulating electrodes may be based on the distance of one or more electrodes in the subset electrodes from the phrenic nerve 222. For example, if an electrode is a distance less than or equal to the stimulation radius R (which may be based on the strength of the resulting magnet field), then the phrenic nerve 222 may be effectively stimulated by a current traveling to that electrode 212A-C. In the example shown in FIG. 3, one electrode 212A is within the stimulating radius R of the phrenic nerve 222. Thus, electrode 212A is positioned to effectively stimulate the phrenic nerve 222. For example, a stimulation pulse between electrode 212A and either 212B or 212C may stimulate the phrenic nerve 222. In the example shown, the most effective subset of electrodes to stimulate the phrenic nerve 222 is a stimulation pulse between electrodes 212A and 212B (the two electrodes positioned closest to the phrenic nerve) because the resulting magnetic field is generated closer to the phrenic nerve 222. In an example, electrodes 212A and 212B may have opposite polarities while the remaining electrode 212C is not carrying a charge. In another example, all electrodes 212A-C are assigned a charge.

As shown in FIG. 2F, the deformable segment 210 of the stimulation lead 200 includes three electrodes 212A-C. Although three electrodes 212A-C are shown, it should be appreciated that any number of electrodes may be included in the deformable segment 210. For example, the deformable segment 210 may include two to twelve electrodes. The electrodes 212A-C may be evenly distributed about the deformable segment 210. Alternatively, the electrodes 212A-C may be unevenly distributed. Additionally or alternatively, the electrodes 212A-C may be distributed about the deformable segment 210 based on the non-elongate shape of the deformable segment 210. For example, electrodes 212A-C may be positioned along corners and/or edges of a deformable segment 210 with a non-elongate shape having at least one edge and/or corner. Additionally or alternatively, the electrodes 212A-C may be a variety of shapes and sizes. Each electrode 212A-C may be the same shape and/or size. Alternatively, each electrode 212A-C may have a different shape/size.

Figure 3:
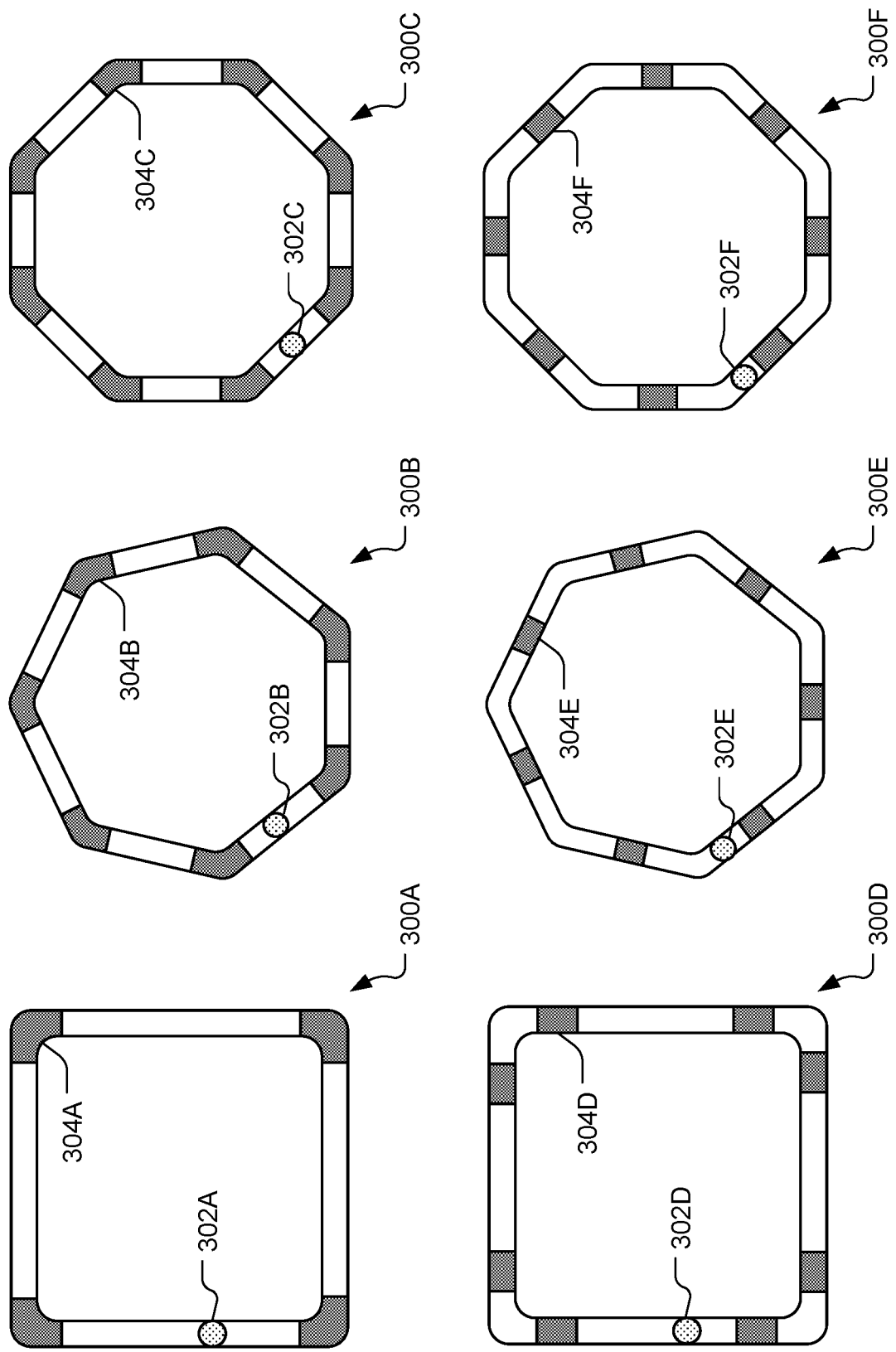
FIG. 3 shows example non-elongate shape configurations for a deformable segment of a stimulation lead.

FIG. 3 shows example non-elongate shape configurations 300A-F for a deformable segment of a stimulation lead. The shape configuration 300A-F may be coupled to a stimulation lead at a bend 302A-F, as described herein. As additionally described herein, there may be a variety of non-elongate shapes of a deformable segment of the stimulation lead. For example, as shown, the non-elongate shape configuration 300A-F may be a polygon. In example, the non-elongate shape configuration 300A-F may be a rectangle (for example, shape configurations 300A, D), an odd-sided polygon (for example, the heptagon shown in shape configurations 300B, E) or an even-sided polygon (for example, the octagon shown in shape configurations 300C, F). The electrodes 304A-F (as shown as shaded portions of the shape configurations 300A-F) may be distributed about the shape configuration 300A-F evenly or unevenly. In an example, the electrodes 304A-C may be positioned at or around corners of the shape configurations 300A-C. In another example, the electrodes 304D-F may be positioned at or around sides or edges of the shape configuration 300D-F. There may be any number of electrodes 304A-F along the shape configuration 300A-F. The quantity of electrodes 304A-F may be proportional to the number of corners and/or edges of the shape configuration 300A-F.

FIG. 4 shows an anatomy of a human patient 400 with placement of a stimulation lead 422. The elements of the patient 400 may be similar to that described for the patient 100 in FIG. 1. As shown, the body 402 of the patient 400 includes a right phrenic nerve 404A, a left phrenic nerve 404B, a diaphragm 406, a right internal jugular vein 408A, a left internal jugular vein 408B, a right brachiocephalic vein 410A, a left brachiocephalic vein 410B, a right subclavian vein 412A, a left subclavian vein 412B, a right jugular-brachiocephalic junction 414A, a left jugular-brachiocephalic junction 414B, a superior vena cava (SVC) 416, a SVC junction 418, and a heart 420. Although not shown, the body 402 of the patient 400 contains other anatomical structures.

Unlike FIG. 1, FIGS. 4A and 4B show a stimulation lead 422 intravenously placed in the body 402. The stimulation lead 422 may have similar features to stimulation leads described herein (e.g., stimulation lead 200). The stimulation lead 422 may include a first deformable segment 426 and second deformable segment 430 which may be similar to, or the same as, deformable segments described herein (e.g., deformable segments 210, 214, 300A-F). The stimulation may also include a first elongate segment 424 and a second elongate segment 428 which may each be similar to, or the same as, elongate segments described herein (e.g., first elongate segment 216A and second elongate segment 216B).

The stimulation lead may be implanted in the body 402. A portion of the blood vessel in which at least a portion of the stimulation lead 422 is placed is proximate a phrenic nerve (e.g., right phrenic nerve 404A or left phrenic nerve 404B, as shown by dotted lines in FIGS. 4A-B). In the example shown, at least a portion of the stimulation lead 422 is placed in the left subclavian vein 412B near the left jugular-brachiocephalic junction 414B, proximate the left phrenic nerve 404B. A first deformable segment 426 of the stimulation lead 422 has a spiral non-elongate configuration inside the left subclavian vein 412B. Alternatively, the first deformable segment 426 of the stimulation lead 422 may have a planar, circular configuration inside the left subclavian vein 412B. Although a deformable segment of the stimulation lead 422 is shown in the left subclavian vein 412B, it should be appreciated that the deformable segment of the stimulation lead 422 may be positioned in any blood vessel in the body 402 that runs proximate a phrenic nerve (e.g., the right internal jugular vein 408A, the left internal jugular vein 408B, the right brachiocephalic vein 410A, the left brachiocephalic vein 410B, the right subclavian vein 412A, the left subclavian vein 412B, the right jugular-brachiocephalic junction 414A, the left jugular-brachiocephalic junction 414B, SVC 416, SVC junction 418, carotid arteries, subclavian arteries, aorta, etc.).

The stimulation lead 422 may also include a second deformable segment 430, as shown in FIG. 4A. The stimulation lead 422 in FIG. 4A may be similar to the shape configuration of the stimulation lead 200 shown in FIGS. 2B-C. The second deformable segment 430 may be placed remote (or removed) from a phrenic nerve. Additionally or alternatively, the second deformable segment 430 may or may not include electrodes. The first deformable segment 426 and the second deformable segment 430 may be coupled via the second elongate segment 428. The first deformable segment 426 and the second deformable segment 430 may be positioned any distance apart. In another example, more than one stimulation lead 422 may be positioned in the body 402 of the patient 400. For example, a first stimulation lead may target the right phrenic nerve 404A and a second stimulation lead may target the left phrenic nerve 404B. Alternatively, one stimulation lead 422 may target both phrenic nerves. As shown in FIG. 4B, a portion of the stimulation lead 422 may run proximate both the right phrenic nerve 404A and the left phrenic nerve 404B and may be used to stimulate both phrenic nerves. The stimulation lead 422 in FIG. 4B may be similar to the shape configuration of the stimulation lead 200 shown in FIG. 2D, including a first deformable segment 210 and a second elongate portion 216B, without a second deformable segment 214. In either of the configurations shown in FIGS. 4A-B, one or both phrenic nerves may be stimulated for effective pacing of the diaphragm muscles.

The stimulation lead 422 may be placed inside the body 402 in an elongate configuration (e.g., using a stylet), as described herein. Additionally, the stimulation lead 422 may be fixed or secured in a blood vessel by one or more fixation elements, as described herein. The fixation element may be located on the first elongate segment 424 of the stimulation lead 422. The stimulation lead 422 may be stabilized by one or more deformable segments of the stimulation lead 422 configured to contact an interior wall of the blood vessel.

The stimulation lead 422 is capable of providing voltage to one or more electrodes coupled to the stimulation lead 422 from a power source. As described herein, attributes of each electrode along the stimulation lead may be individually addressable and controllable by a controller (such as a PCB). In an example, a clinician may control the nerve pacing of the stimulation lead 422 via a controller, and observe the resultant ventilatory efforts of the patient at the ventilator. The controller may be a component of the ventilator, or may be a separate device. In an example where the controller is integrated into the ventilator, the power source is provided by the ventilator. In an example where the controller is a separate device, the controller may be associated with a display and user interface to allow viewing or selecting of electrode attributes.

Figure 5:
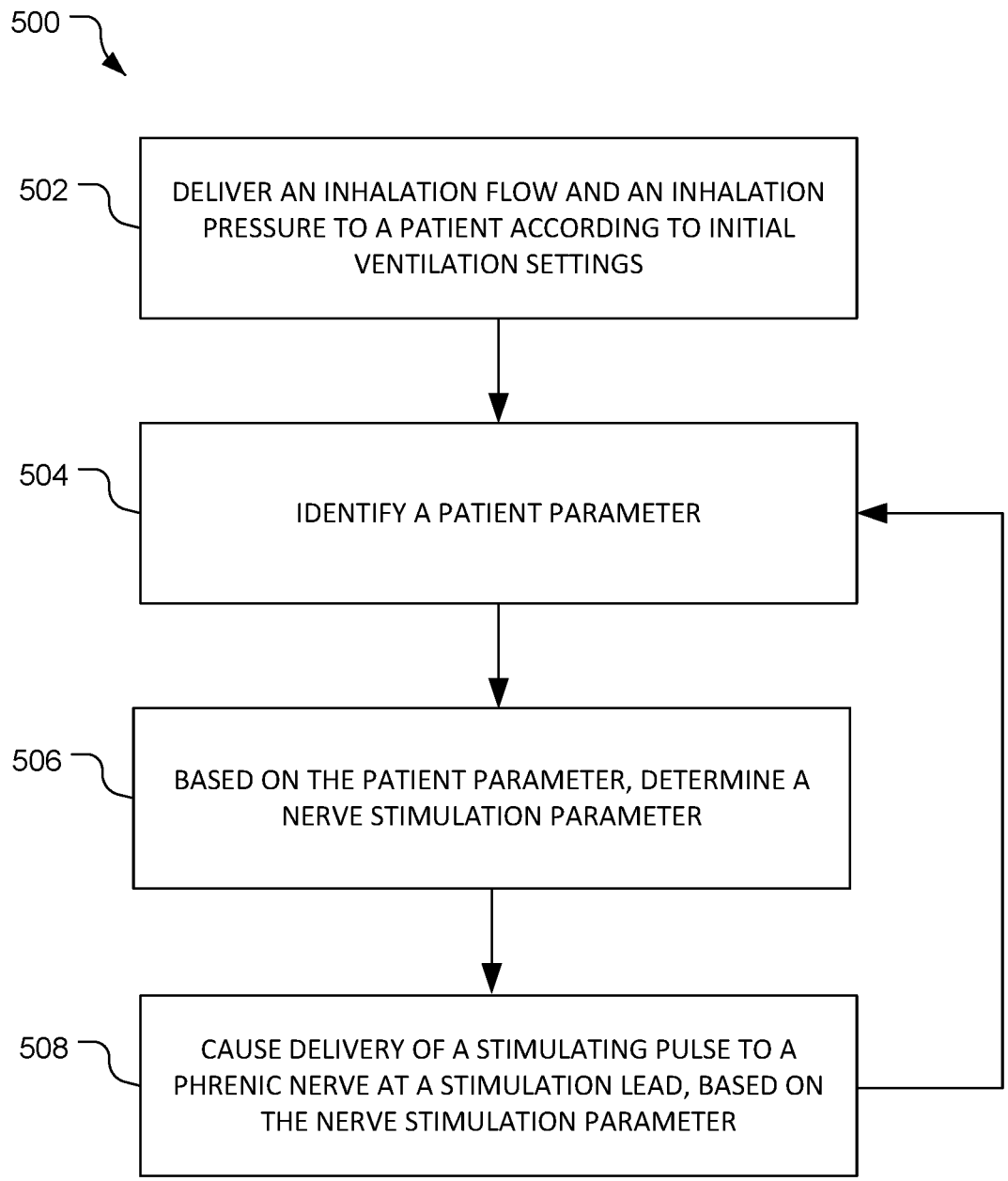
FIG. 5 shows an example method for phrenic nerve stimulation.
Figure 6:
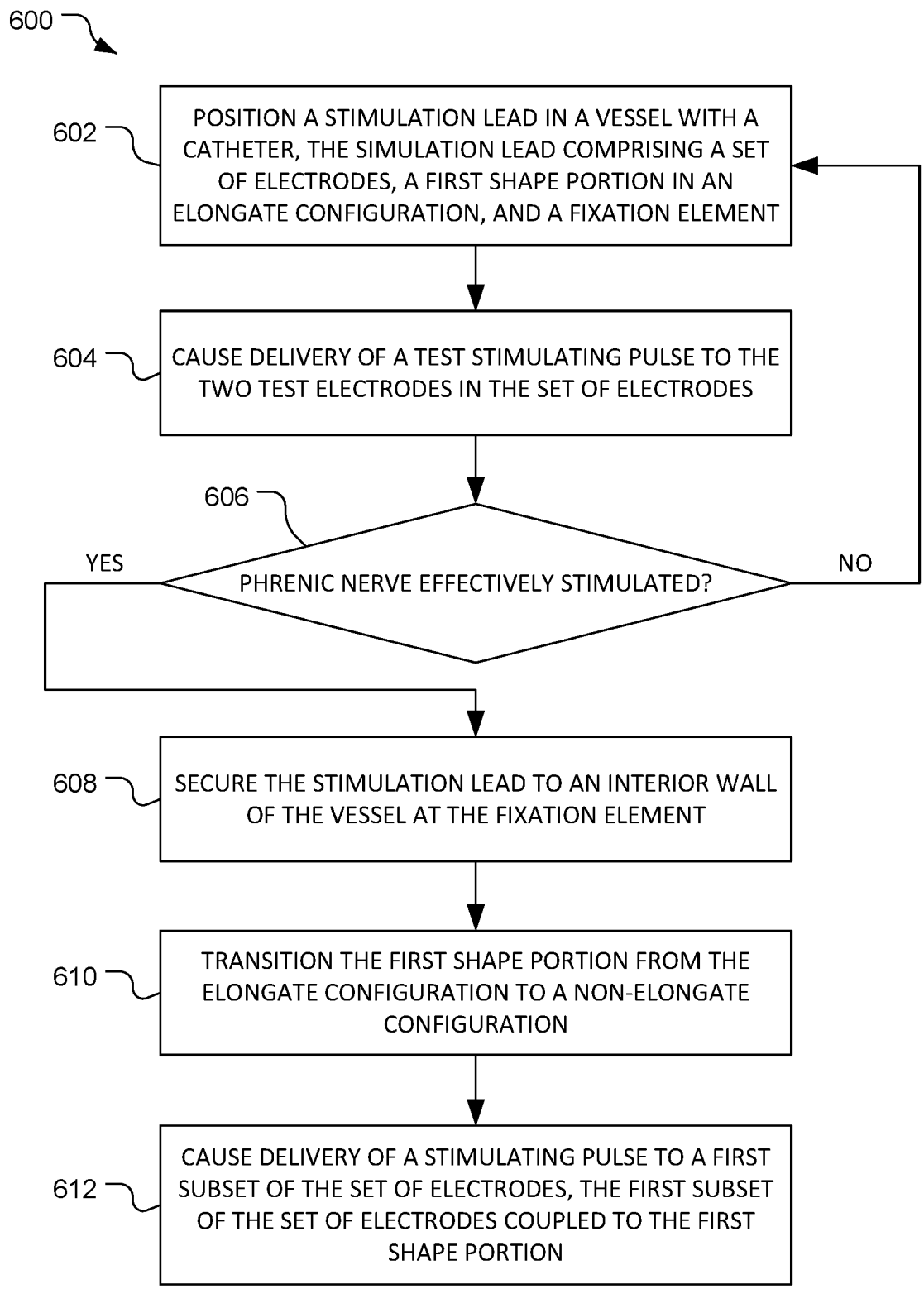
FIG. 6 shows another example method for phrenic nerve stimulation.

FIGS. 5-6 show example methods according to the technology described herein. The example methods include operations that may be implemented or performed by the systems and devices disclosed herein. For example, a ventilator as described in either FIGS. 7-8 may perform the operations described in the methods. In addition, instructions for performing the operations of the methods disclosed herein may be stored in a memory of a ventilator (e.g., system memory 712 and 808 described in FIGS. 7-8). Further, reference to a stimulation lead in the example methods may be similar to aspects of the stimulation leads described herein (e.g., stimulation lead 200 and stimulation lead 422).

FIG. 5 shows an example method for phrenic nerve stimulation. At operation 502, an inhalation flow and an inhalation pressure may be delivered to a patient. In an example, a ventilator (e.g., ventilator 700, 802) may deliver the inhalation flow and the inhalation pressure. The ventilator may be electrically coupled with a stimulation lead. The stimulation lead may be placed in a blood vessel inside a body of a patient. The stimulation lead may be similar to, or the same as, stimulation leads described herein.

At operation 504, a patient parameter may be identified. The patient parameter may be identified by the ventilator (e.g., measured, calculated, determined, etc.) or may be provided by a clinician. The patient parameter may be associated with the initial ventilation settings and/or delivery performed in operation 502. For example, the patient parameter may be a breathing mode (e.g., spontaneous breath mode or mandatory breath mode), respiratory rate, predicted body weight, patient effort, tidal volume, inspiratory time, expiratory time, peak inspiratory flow, peak circuit pressure, flow pattern, PEEP, lung compliance, lung resistance, or any other patient parameter associated with a breathing pattern of a patient and/or a patient's diaphragm muscle activity not limited to the aforementioned list.

At operation 506, a nerve stimulation parameter may be determined based on the identified patient parameter. In an example, the ventilator may determine the nerve stimulation parameter. The nerve stimulation parameter may be a parameter associated with stimulating at least one phrenic nerve of the patient, such as stimulation rate (i.e., frequency of stimulation pulses), amount of stimulation (e.g., amount of voltage delivered to two or more electrodes on the stimulation lead and/or amount of current between two or more electrodes on the stimulation lead), location of stimulation (e.g., which electrodes are provided voltage), an attribute of an electrode (as further described herein), etc. Additionally, the nerve stimulation parameter may be associated with the current ventilation settings and/or current breath delivery performed by the ventilator. The nerve stimulation parameter may change with a change in the patient parameter. For example, the timing of spontaneous breaths and/or mandatory breaths may be coordinated with delivery of stimulation pulses, thus the stimulation rate may change in association with breathing mode. Additionally or alternatively, the amount of stimulation may vary based on the breathing mode. For example, the amount of stimulation may be specified in association with mandatory breaths. In another example, the amount of stimulation may vary from breath-to-breath in association with spontaneous breaths based on the patient's effort and/or length and/or frequency of inhalation.

In another example, the nerve stimulation parameter may be associated with a predicted body weight of the patient. For example, a lower predicted body weight may be associated with a lesser amount of stimulation. Additionally or alternatively, a higher predicted body may be associated with a larger amount of stimulation. In another example, the predicted body weight of the patient may be associated with a desired respiratory rate and/or stimulation rate. In yet another example, the tidal volume of the patient may be associated with a nerve stimulation parameter. For example, a nerve stimulation parameter may be changed to increase or decrease the patient's tidal volume. In an example, if the tidal volume is too low, the tidal volume may be increased by increasing the amount of stimulation of the phrenic nerve. In an example, the amount of stimulation may be associated with a desired tidal volume of the patient. It should be appreciated that the nerve stimulation parameter may be determined based on any other patient parameter.

In another example, updated ventilation settings may be determined based on the patient parameter and the nerve stimulation parameter. In an example, the ventilator may determine the updated ventilation settings. In another example, the updated ventilation settings may be associated with an increase or a decrease in at least one of: the inhalation flow or the inhalation pressure. As a patient's diaphragm is more active, the inhalation flow and/or the inhalation pressure may be decreased. The updated ventilation settings may be based on a patient parameter and adjusted based on the determined nerve stimulation parameter. In a further example, the settings difference between the initial ventilation settings (at operation 502) and the updated ventilation settings is based on the nerve stimulation parameter.

In an instance where the ventilator is also updating ventilation settings based on the nerve stimulation parameter, it should be appreciated that the identification of a patient parameter, the determination of a nerve stimulation parameter, and updating ventilation settings may be determined in any order. In an example, the nerve stimulation parameter and updated ventilation settings are determined in a closed-loop system. For example, the nerve stimulation parameter and updated ventilation settings may be associated with each other. Updated flow and an updated pressure may be delivered according to the updated ventilation settings. In an example, a ventilator may deliver the updated ventilation settings. In an example, the inhalation flow and/or inhalation pressure delivered at operation 502 may be changed to the updated ventilation settings.

At operation 508, delivery of a stimulating pulse may be caused based on the nerve stimulation parameter. The stimulating pulse may be causing during delivery of an inhalation phase by the ventilator. As described herein, delivery of a stimulating pulse stimulates a nearby phrenic nerve. Delivery of the stimulating pulse may be caused by providing a voltage to the electrodes on the stimulation lead. The voltage provided to two or more electrodes result in a current between the two electrodes. The current and resulting magnetic field results in stimulation of a nearby phrenic nerve. Other nerve stimulation parameters described herein may be associated with the stimulation amount, stimulation rate, stimulation length, electrode attributes, and/or stimulation location.

In an example, delivery of the stimulating pulse may be associated with the patient's efforts (e.g., coordinated in timing of delivery of stimulating pulse and/or amount of stimulation). In an example, delivery of the stimulating pulse may be postponed until after observing the patient. In another example, aspects of the stimulating pulse may be determined with the nerve stimulation parameter at operation 506.

In another example, the stimulating pulse may be timed according to a triggering strategy. The ventilator delivering the updated flow and update pressure according to the updated ventilator settings may also cause delivery of the stimulating pulse. The stimulating pulse may be coordinated with an inhalation phase of a patient. For example, the stimulating pulse may be coordinated with delivery of the updated flow and updated pressure.

When delivering stimulating pulses according to a triggering strategy, the stimulating pulse may be delivered at the time of the trigger. In another example, the stimulating pulse may be delayed from the trigger or may be delivered prior to the trigger. In another example, the stimulating pulse may be delivered over a period of time that may include the time of the trigger. Delivery of the stimulating pulse based on triggering allows pacing of diaphragm muscles in association with the trigger.

In a flow triggering strategy, the patient's inspiration effort is detected when the measured patient exhalation flow value drops below a flow baseline (i.e., the base flow) by a set amount (based on the triggering sensitivity). In a pressure triggering strategy or pressure trigger type, the patient's inspiration effort is detected when the measured expiratory pressure value drops below a pressure baseline (for example, the set PEEP level) by a set amount (based on triggering sensitivity). Another parameter that can be used for a triggering strategy trigger type is a derived signal, such as an estimate of the intrapleural pressure of the patient and/or the derivative of the estimate of the patient's intrapleural pressure. The term "intrapleural pressure," as used herein, refers generally to the pressure exerted by the patient's diaphragm on the cavity in the thorax that contains the lungs, or the pleural cavity. The derivative of the intrapleural pressure value will be referred to herein as a "Psync" value that has units of pressure per time. An example of triggering and cycling based on the Psync value is provided in U.S. patent application Ser. No. 16/411,916 ("the '916 Application"), titled "Systems and Methods for Respiratory Effort Detection Utilizing Signal Distortion" and filed on May 14, 2019, which is incorporated herein by reference in its entirety. That triggering strategy discussed in the '916 Application is referred to herein as the "signal distortion" triggering strategy or "signal distortion" trigger type. As discussed in the '916 Application, the signal distortion triggering strategy may operate on the Psync signal or other signals, such as flow or pressure.

As required or desired, the method 500 may repeat operations 504-508 as additional patient parameters are identified and/or with a change in the identified patient parameter. For example, a change in the identified patient parameter at operation 504 may result in a change in the nerve stimulation parameter and/or updated ventilation settings. Repeating steps 504-508 may occur at any interval of time, such as specified increments of time (e.g., 5 ms) or from breath-to-breath, etc. In one example, as the patient's efforts increase, the ventilator may decrease an amount of stimulation of the phrenic nerve and/or decrease a delivered flow and/or pressure during the inhalation phase.

FIG. 6 shows another example method for phrenic nerve stimulation. At operation 602, a stimulation lead may be positioned in a blood vessel while in an elongate configuration, the stimulation lead comprising a set of electrodes, a first deformable segment, and a fixation element. The stimulation lead may be similar to stimulation leads described herein. The set of electrodes may be distributed along the first deformable segment and/or may be positioned along the stimulation lead outside of the first deformable segment. For example, electrodes may be positioned on an elongate segment coupled to the first deformable segment. Each electrode may have similar characteristics of electrodes described herein. The fixation element may be similar to fixation elements described herein. In examples, when the stimulation lead is being placed in the blood vessel, a stylet may be inserted into the stimulation lead to straighten the deformable segment into an elongate configuration. In examples, the blood vessel may be a vein at least a portion of which is located adjacent a phrenic nerve. The stimulation lead may include a variety of other elements, such as one or more elongate segments, additional deformable segments, etc., as described herein.

At operation 604, delivery of a test stimulating pulse to at least two test electrodes in the set of electrodes may be caused. The delivery of the test stimulating pulse may be caused by a controller. The controller may be commanded by a ventilator or a clinician. Aspects of the stimulating pulse (e.g., stimulation frequency, amount of stimulation, etc.) or attributes of the at least two test electrodes may be controlled independently, as further described herein. The ventilator may perform a negative inspiratory force (NIF) maneuver while delivering the stimulating pulse. The NIF maneuver is a coached maneuver where the patient is prompted to draw a maximum inspiration against an occluded airway (when the inhalation valve and exhalation valve are fully closed). Performing the NIF maneuver while delivered the stimulating pulse may allow more accurate estimations of the force generated by the stimulating pulse. Better estimations of the force generated by the stimulating pulse may assist in determination of the stimulation lead placement in the body, selection of electrodes used to stimulate the phrenic nerve, or any other pacing parameter.

At determination 606, effective stimulation of the phrenic nerve is evaluated. For example, a clinician or surgeon may determine if the phrenic nerve was effectively stimulated during delivery of the stimulating pulse at operation 606. In an example, a patient's bodily reaction to the stimulating pulse may be used in the determination. For example, a clinician may evaluate feedback of the patient's diaphragm muscles in response to the stimulating pulse. Alternatively, a ventilator may determine if the phrenic nerve was effectively stimulated during the test stimulating pulse. For example, the ventilator may receive data associated with the patient's effort or tidal volume caused by the test stimulating pulse. The evaluation of effective stimulation, by a human or the ventilator, may be obtained using visual information (e.g., rise and fall of the patient's chest), a determined pressure and/or flow in the breathing circuit, diaphragm muscle activity information, or any other information related to stimulation of the phrenic nerve to cause stimulation of diaphragm muscles.

In examples, the determination 606 is binary (e.g., whether the phrenic nerve has been effectively stimulated) or may be based on a threshold (e.g., whether the stimulating pulse caused at least a specified amount of stimulation of the phrenic nerve). If it is determined that the phrenic nerve is not effectively stimulated, flow branches to "NO" and operations 602-606 may be repeated. For example, the stimulation lead may be repositioned in the blood vessel until the test stimulating pulse effectively stimulates the phrenic nerve. In examples, this process may be referred to as mapping an effective position of the stimulation lead in the blood vessel. In examples, the test stimulating pulse may be continuous while operations 602-606 repeat. If, after repositioning the stimulation lead in the blood vessel and/or changing pacing parameters, the phrenic nerve remains to be not effectively stimulated, the stimulating pulse may be supported by the ventilator. For example, the ventilator may provide pressure support, automatic tube compensation, proportional assist ventilation, or any other support techniques to supplement the tidal volume delivered to the patient while delivering a stimulating pulse.

If, however, it is determined that the phrenic nerve is effectively stimulated, flow branches "YES" to operation 608. At operation 608, the stimulation lead may be secured to an interior wall of the blood vessel at the fixation element. In examples, the fixation element may have a rotatable element to affix the stimulation lead to the interior wall of the blood vessel, as described herein.

At operation 610, the deformable segment may be transitioned from the elongate configuration to a non-elongate configuration. In an example, this transition may be facilitated by retracting a stylet from the stimulation lead to allow the deformable segment to return to a non-elongate configuration. The stylet may be completely retracted or partially retracted. The non-elongate shape of the deformable segment may be based on an amount of retraction of the stylet. As described herein, the non-elongate configuration of the first deformable segment may be a variety of shapes. The non-elongate configuration may be substantially planar (e.g., a circle) or may be non-planar (e.g., a spiral). One or more portions of the first deformable segment in the non-elongate configuration may contact the interior wall of the blood vessel. In examples, the non-elongate configuration may provide stability of the stimulation lead inside the blood vessel in addition to the fixation element. Thus, the stimulation lead may be implanted in a patient.

In an example, the stimulation lead includes additional deformable segments (e.g., a second deformable segment, a third deformable segment, etc.). Additional deformable segments may be transitioned to their respective non-elongate configurations at the same time as the first deformable segment. Alternatively, additional deformable segments may be transitioned to their respective non-elongate configurations at a different time than the first deformable segment (e.g., as a stylet is removed from each deformable segment). The non-elongate configuration of each additional deformable segment may be different or the same as the first deformable segment. For example, the first deformable segment may be a spiral or helix while a second deformable segment is a circle. In another example, the first deformable segment and the second deformable segment may each be a circle.

At operation 612, delivery of the stimulating pulse to a first subset of the set of electrodes may be caused, the first subset of the set of electrodes coupled to the first deformable segment. In an example, the first deformable segment may include at least two electrodes. In a further example, at least one electrode exists outside the first deformable segment (e.g., on an elongate segment of the stimulation lead or on an additional deformable segment of the stimulation lead). The first subset of electrodes may be distributed along the first deformable segment, as described herein. In an example where the stimulation lead includes additional deformable segments, one or more of the additional deformable segments may not include an electrode. Alternatively, one or more of the additional deformable segments may include at least one electrode. For example, a second deformable segment may include no electrodes. In another example, a second deformable segment may include a second subset of the set of electrodes. For instance, the second deformable segment may include between 2-12 electrodes.

Aspects of delivering the stimulating pulse may be similar to, or the same as, one or more operations described in method 500 in FIG. 5. For example, aspects of the stimulating pulse (e.g., timing, amount, etc.) and/or attributes of the set of electrodes may be controlled by a ventilator. In an example, a ventilator may coordinate delivery of stimulating pulses with patient parameters and/or ventilation settings. In a further example, delivery of the stimulating pulse may be associated with an inhalation phase of a patient being actively ventilated by a ventilator. Alternatively, aspects of the stimulating pulse (e.g., timing, amount, etc.) may be controlled by another device and/or a clinician.

Figure 7:
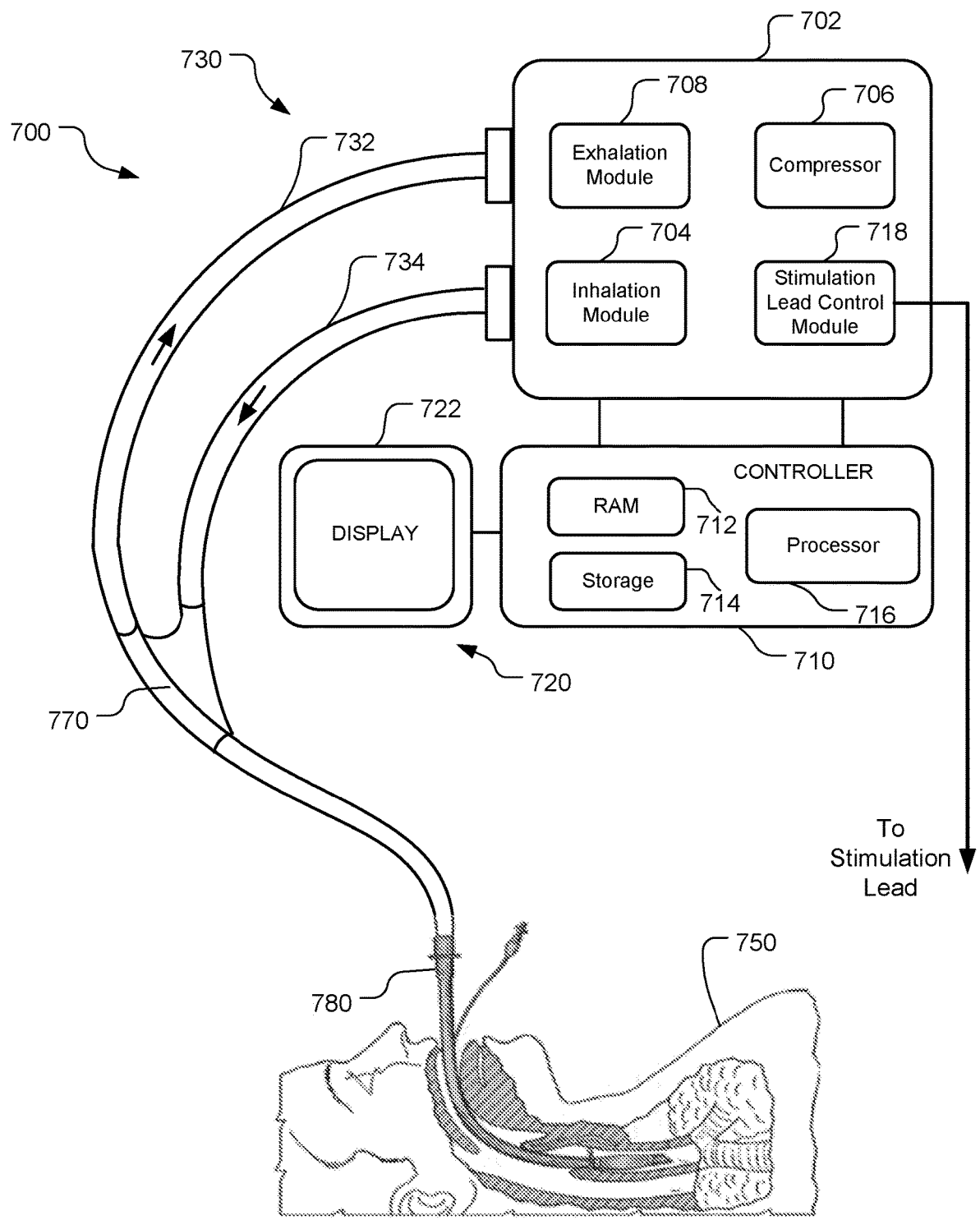
FIG. 7 is a diagram illustrating an example of a ventilator connected to a human patient and a stimulation lead.

FIG. 7 is a diagram illustrating an example of a ventilator 700 connected to a human patient 750 and a stimulation lead. Ventilator 700 includes a pneumatic system 702 (also referred to as a pressure generating system 702) for circulating breathing gases to and from patient 750 via the ventilation tubing system 730, which couples the patient to the pneumatic system via an invasive (e.g., endotracheal tube, as shown) or a non-invasive (e.g., nasal mask) patient interface.

Ventilation tubing system 730 may be a two-limb (shown) or a one-limb circuit for carrying gases to and from the patient 750. In a two-limb example, a fitting, typically referred to as a "wye-fitting" 770, may be provided to couple a patient interface 780 to an inhalation limb 734 and an exhalation limb 732 of the ventilation tubing system 730.

Pneumatic system 702 may have a variety of configurations. In the present example, system 702 includes an exhalation module 708 coupled with the exhalation limb 732 and an inhalation module 704 coupled with the inhalation limb 734. Compressor 706 or other source(s) of pressurized gases (e.g., air, oxygen, and/or helium) is coupled with inhalation module 704 to provide a gas source for ventilatory support via inhalation limb 734. Stimulation lead control module 718 may provide voltage to a stimulation lead as described herein. The pneumatic system 702 may include a variety of other components, including mixing modules, valves, sensors, tubing, accumulators, filters, etc.

Controller 710 is operatively coupled with pneumatic system 702, signal measurement and acquisition systems, and an operator interface 720 that may enable an operator to interact with the ventilator 700 (e.g., change ventilator settings, select operational modes, view monitored parameters, etc.). Controller 710 may include memory 712, one or more processors 716, storage 714, and/or other components of the type found in command and control computing devices. In the depicted example, operator interface 720 includes a display 722 that may be touch-sensitive and/or voice-activated, enabling the display 722 to serve both as an input and output device.

The memory 712 includes non-transitory, computer-readable storage media that stores software that is executed by the processor 716 and which controls the operation of the ventilator 700. In an example, the memory 712 includes one or more solid-state storage devices such as flash memory chips. The processor 716 may be configured to control attributes of the electrodes on a stimulation lead. In an alternative example, the memory 712 may be mass storage connected to the processor 716 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 716. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory system or between the ventilatory system and other therapeutic equipment and/or remote monitoring systems may be conducted over a distributed network, as described further herein, via wired or wireless means. Further, the present methods may be configured as a presentation layer built over the TCP/IP protocol. TCP/IP stands for "Transmission Control Protocol/Internet Protocol" and provides a basic communication language for many local networks (such as intra- or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Figure 8:
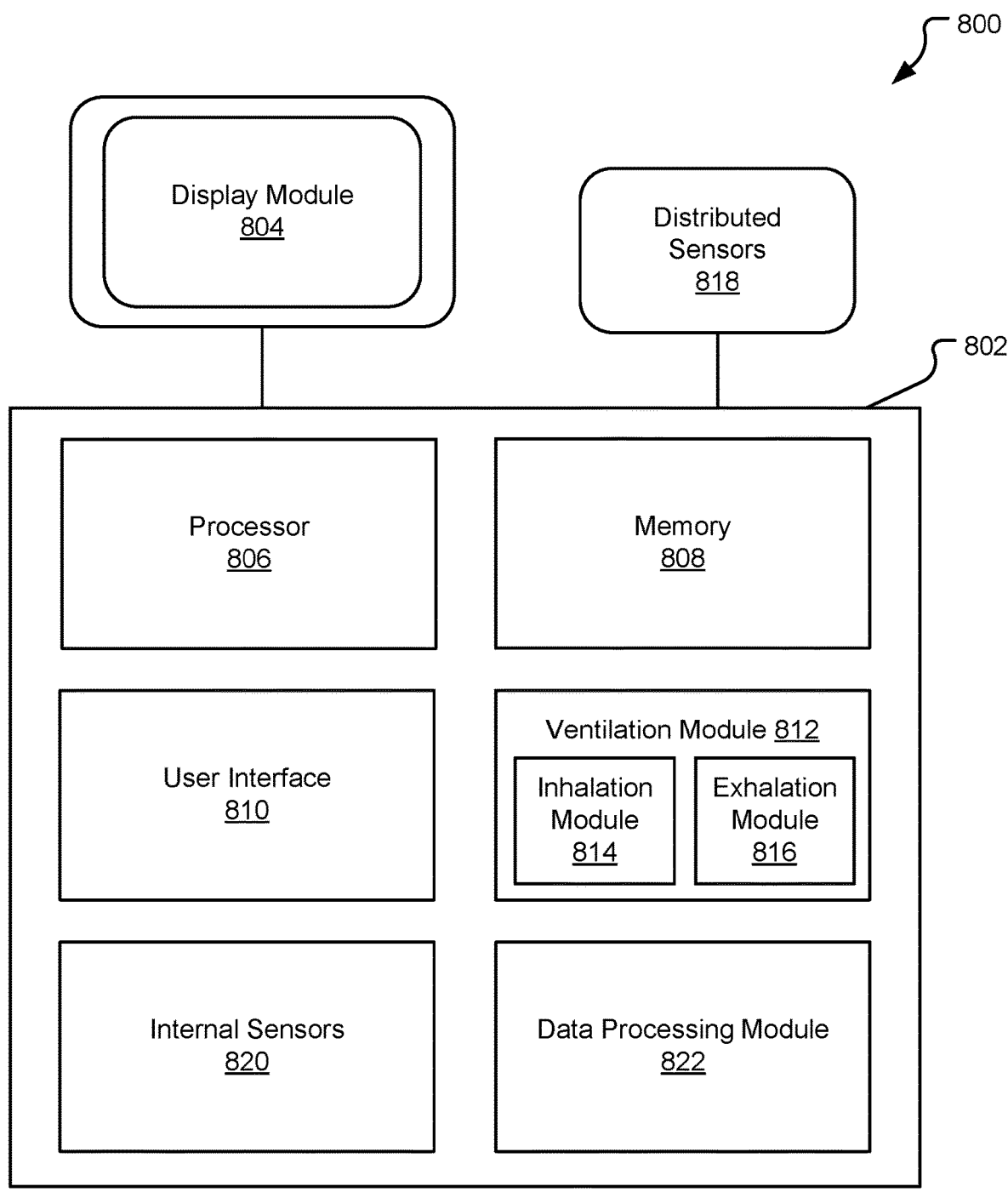
FIG. 8 is a block-diagram illustrating an example of a ventilatory system.

FIG. 8 is a block-diagram illustrating an example of a ventilatory system 800. Ventilatory system 800 includes ventilator 802 with its various modules and components. That is, ventilator 802 may further include, among other things, memory 808, one or more processors 806, user interface 810, and ventilation module 812 (which may further include an inhalation module 814 and an exhalation module 816). Memory 808 is defined as described above for memory 808. Similarly, the one or more processors 806 are defined as described above for one or more processors 806. Processors 806 may further be configured with a clock whereby elapsed time may be monitored by the system 800.

The ventilation system 800 may also include a display module 804 communicatively coupled to ventilator 802. Display module 804 provides various input screens, for receiving input, and various display screens, for presenting useful information. Inputs may be received from a clinician. The display module 804 is configured to communicate with user interface 810 and may include a graphical user interface (GUI). The GUI may be an interactive display, e.g., a touch-sensitive screen or otherwise, and may provide various windows (i.e., visual areas) comprising elements for receiving user input and interface command operations and for displaying ventilatory information (e.g., ventilatory data, alerts, patient information, parameter settings, modes, etc.). The elements may include controls, graphics, charts, tool bars, input fields, icons, etc. Alternatively, other suitable means of communication with the ventilator 802 may be provided, for instance by a wheel, keyboard, mouse, or other suitable interactive device. Thus, user interface 810 may accept commands and input through display module 804. Display module 804 may also provide useful information in the form of various ventilatory data regarding the physical condition of a patient and/or a prescribed respiratory treatment. The useful information may be derived by the ventilator 802, based on data collected by a data processing module 822, and the useful information may be displayed in the form of graphs, wave representations (e.g., a waveform), pie graphs, numbers, or other suitable forms of graphic display. For example, the data processing module 822 may be operative to determine ventilation settings (otherwise referred to as ventilatory settings, or ventilator settings) associated with a nerve stimulation lead, etc., as detailed herein.

Ventilation module 812 may oversee ventilation of a patient according to ventilation settings. Ventilation settings may include any appropriate input for configuring the ventilator to deliver breathable gases to a particular patient, including measurements and settings associated with exhalation flow of the breathing circuit. Ventilation settings may be entered, e.g., by a clinician based on a prescribed treatment protocol for the particular patient, or automatically generated by the ventilator, e.g., based on attributes (i.e., age, diagnosis, ideal body weight, predicted body weight, gender, ethnicity, etc.) of the particular patient according to any appropriate standard protocol or otherwise, such as may be determined in association with stimulating a phrenic nerve with a stimulation lead. In some cases, certain ventilation settings may be adjusted based on the exhalation flow, e.g., to optimize the prescribed treatment.

Ventilation module 812 may further include an inhalation module 814 configured to deliver gases to the patient and an exhalation module 816 configured to receive exhalation gases from the patient, according to ventilation settings that may be based on the exhalation flow. As described herein, inhalation module 814 may correspond to the inhalation module 704 and 814, or may be otherwise coupled to source(s) of pressurized gases (e.g., air, oxygen, and/or helium), and may deliver gases to the patient. As further described herein, exhalation module 816 may correspond to the exhalation module 708 and 816, or may be otherwise coupled to gases existing the breathing circuit.

Figure 9:
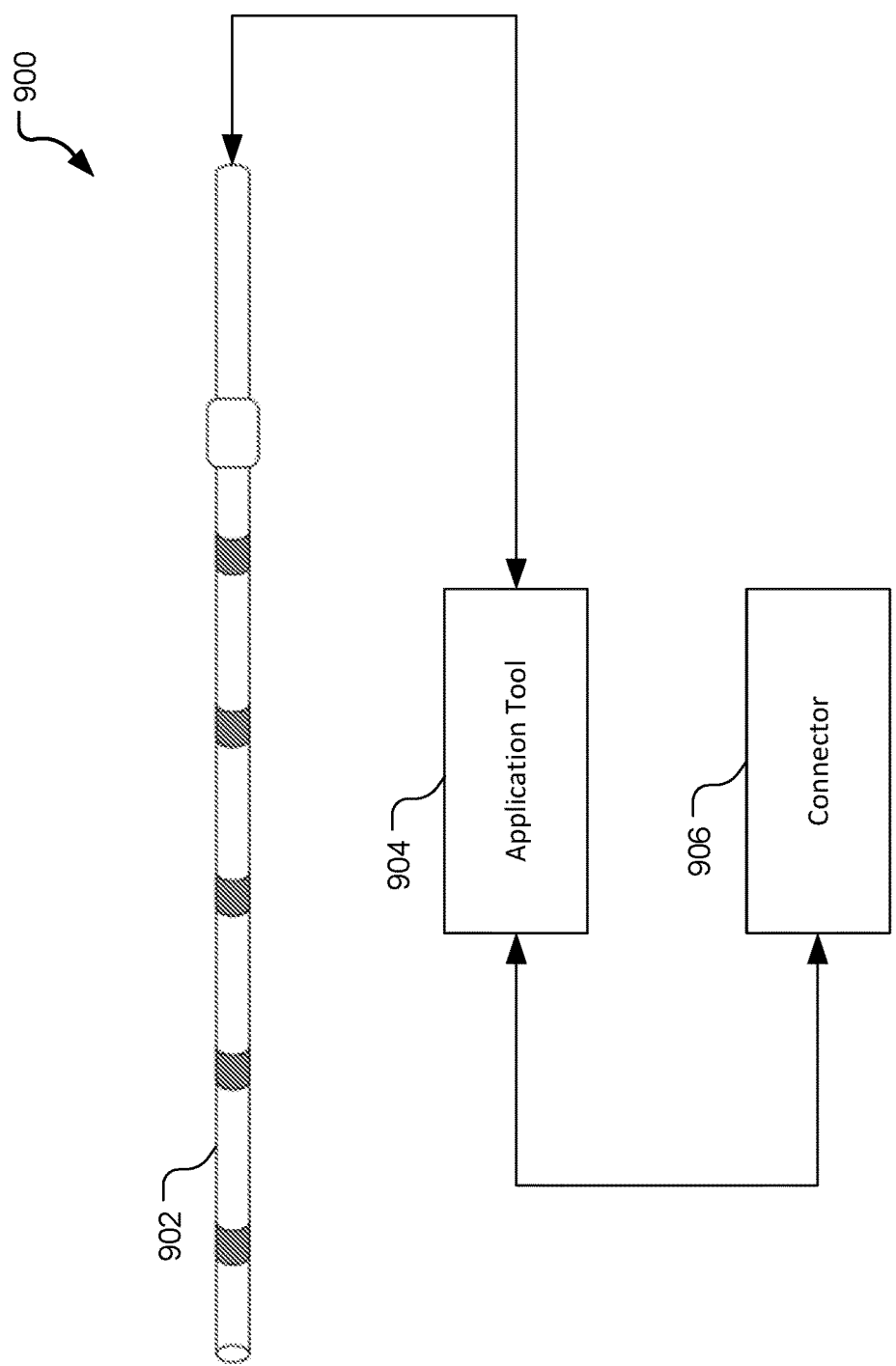
FIG. 9 is an example catheter system.

FIG. 9 is an example catheter system 900 including a stimulation lead 902, an application tool 904, and a connector 906. The stimulation lead 902 shares aspects with the stimulation leads described herein (e.g., stimulation lead 200 and stimulation lead 422). The application tool 904 is any tool known in the art capable of assisting with inserting, implanting, removing, or otherwise moving the stimulation lead within the body of the patient while the application tool 904 remains outside of the body of the patient. The application tool 904 enables a stylet to be inserted into, removed from, or otherwise moved inside of the stimulation lead 902 to cause the stimulation lead 902 to change shape (e.g., transition between an elongate configuration and a non-elongate configuration, as described herein).

The connector 906 may be any connector known in the art capable of including independent leads for one or more of the electrodes on the stimulation lead 902. Each lead of the connector 906 may independently energize the electrode to which the lead is electrically coupled. For example, if the stimulation lead has eight electrodes, the connector 906 may have eight independent leads electrically coupled to each of the eight electrodes. The connector 906 may be electrically couplable to a controller to independently energize each electrode on the stimulation lead 902 at each lead. The controller may be a component of a ventilator (e.g., stimulation lead control module 718 of ventilator 702). Alternatively, the controller may be a stand-alone nerve stimulation controller or may be incorporated into some other device such as a patient monitor.

Although the present disclosure discusses the implementation of these techniques in the context of nerve stimulation with a stimulation lead, the techniques introduced above may be implemented for a variety of medical devices or devices utilizing nerve stimulation. A person of skill in the art will understand that the technology described in the context of a medical ventilator for human patients could be adapted for use with other systems such as ventilators for non-human patients or general gas transport systems. Additionally, a person of ordinary skill in the art will understand that the modeled exhalation flow may be implemented in a variety of breathing circuit setups.

Those skilled in the art will recognize that the methods and systems of the present disclosure may be implemented in many manners and as such are not to be limited by the foregoing aspects and examples. In other words, functional elements being performed by a single component or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible.

Functionality may also be, in whole or in part, distributed among multiple components, in manners now known or to become known. Thus, a myriad of software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executed or performed substantially concurrently or in reverse order, depending on the functionality and implementation involved.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurement techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A stimulation lead for stimulating a phrenic nerve, the stimulation lead comprising:
    a first elongate segment defining a center line;
    a fixation element coupled to the first elongate segment, the fixation element configured to removably couple the stimulation lead to an interior wall of a vein;
    a set of electrodes configured to stimulate the phrenic nerve;
    a first deformable segment coupled to the first elongate segment, the first deformable segment including a first subset of electrodes of the set of electrodes, wherein the first deformable segment is configured to transition, when positioned at a targeted location within a body, between at least two configurations comprising:
        a first elongate configuration wherein the first subset of electrodes are distributed substantially along the center line; and
        a first non-elongate configuration wherein the first subset of electrodes are distributed outwardly from the center line; and
    a second elongate segment extending along the center line; and
    a second deformable segment coupled to the second elongate segment, wherein the second deformable segment is configured to transition, independently from the first deformable segment, between at least two configurations comprising:
        a second elongate configuration extending substantially along the center line; and
        a second non-elongate configuration wherein the second deformable segment is configured to be substantially circular.

2. The stimulation lead of claim 1, wherein the first non-elongate configuration is one of: a circle or a helix.

3. The stimulation lead of claim 2, wherein at least one portion of the first deformable segment is configured to contact an interior wall of the vein when the first deformable segment is in the first non-elongate configuration.

4. The stimulation lead of claim 2, wherein the first non-elongate configuration is a circle existing substantially along a plane, the first subset of electrodes includes at least two electrodes, and the first subset of electrodes are evenly distributed about the first deformable segment.

5. The stimulation lead of claim 1, wherein the transition of the first deformable segment between the first elongate configuration and the first non-elongate configuration occurs in response to at least partial retraction of a stylet from the first deformable segment.

6. The stimulation lead of claim 5, wherein, when the first deformable segment is in the first non-elongate configuration, the stimulation lead comprises a bend at the coupling of the first elongate segment and the first deformable segment.

7. The stimulation lead of claim 1, wherein the first elongate segment comprises at least one electrode of the set of electrodes.

8. The stimulation lead of claim 1, the
    wherein at least one portion of the second non-elongate configuration is configured to contact an interior wall of the vein when the second deformable segment is in the second non-elongate configuration.

9. The stimulation lead of claim 8, wherein the first deformable segment is coupled to the first elongate segment and the second elongate segment.

10. The stimulation lead of claim 9, wherein the second elongate segment comprises at least one electrode of the set of electrodes.

11. The stimulation lead of claim 10, wherein the second deformable segment does not include electrodes.

12. A stimulation lead for stimulating a phrenic nerve, the stimulation lead comprising:
    a set of electrodes configured to stimulate the phrenic nerve;
    a first elongate segment defining a center line, wherein the first elongate segment includes at least a first electrode of the set of electrodes;
    a second elongate segment extending along the center line, wherein the second elongate segment includes at least a second electrode of the set of electrodes;
    a proximal deformable segment coupled between the first elongate segment and the second elongate segment, the proximal deformable segment including at least a third electrode and a fourth electrode of the set of electrodes, wherein the proximal deformable segment is configured to transition, when positioned at a targeted location within a body, between at least two configurations comprising:
        an elongate configuration wherein the deformable segment extends substantially along the center line; and
        a non-elongate configuration wherein the third electrode and fourth electrode are positioned outwardly from the center line;
    a distal deformable segment coupled to the second elongate segment, wherein the distal deformable segment is configured to transition, when positioned at a targeted location within the body, between at least two configurations comprising:
        a distal elongate configuration wherein the distal deformable segment extends substantially along the center line; and
        a distal non-elongate configuration wherein the distal deformable segment is substantially circular.

13. The stimulation lead of claim 12, wherein, when the deformable segment is in the non-elongate configuration, the stimulation lead includes a bend between the first elongate segment and the deformable segment.

14. The stimulation lead of claim 12, wherein, when the deformable segment is in the non-elongate configuration, the third electrode and the fourth electrode are positioned along a plane substantially perpendicular to the center line.

15. The stimulation lead of claim 12, wherein the distal deformable segment includes including at least a fifth electrode and a sixth electrode of the set of electrodes.

16. The stimulation lead of claim 12, wherein the distal deformable segment does not include electrodes.

\* \* \* \* \*